(12) United States Patent
Gold et al.

(10) Patent No.: US 6,696,252 B2
(45) Date of Patent: Feb. 24, 2004

(54) HIGH-AFFINITY OLIGONUCLEOTIDE LIGANDS TO VASCULAR ENDOTHELIAL GROWTH FACTOR (VEGF)

(75) Inventors: Larry Gold, Boulder, CO (US); Nebojsa Janjic, Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 378 days.

(21) Appl. No.: 09/860,474

(22) Filed: May 18, 2001

(65) Prior Publication Data

US 2003/0032785 A1 Feb. 13, 2003

Related U.S. Application Data

(63) Continuation of application No. 09/156,824, filed on Sep. 18, 1998, now abandoned, which is a continuation of application No. 08/447,169, filed on May 19, 1995, now Pat. No. 5,811,533, which is a continuation-in-part of application No. 07/714,131, filed on Jun. 10, 1991, now Pat. No. 5,475,096, which is a continuation-in-part of application No. 07/536,428, filed on Jun. 11, 1990, now abandoned, application No. 09/860,474, which is a continuation-in-part of application No. 08/205,515, filed on Mar. 3, 1994, now abandoned, and a continuation-in-part of application No. 07/964,624, filed on Oct. 21, 1992, now Pat. No. 5,496,938.

(51) Int. Cl.[7] .................... C12Q 1/68; C12P 19/84; G01N 33/566; C07K 14/00; C07H 21/02; C07H 21/04

(52) U.S. Cl. .................... 435/6; 435/91.2; 435/196; 436/501; 530/350; 536/22.1

(58) Field of Search .................... 435/6, 91.2, 196; 530/350; 436/501; 536/22.1

(56) References Cited

U.S. PATENT DOCUMENTS

| | | |
|---|---|---|
| 5,270,163 A | 12/1993 | Gold et al. |
| 5,459,015 A | 10/1995 | Janjic et al. |
| 5,476,766 A | 12/1995 | Gold et al. |
| 5,811,533 A | 9/1998 | Gold et al. |
| 5,849,479 A | 12/1998 | Janjic et al. |

FOREIGN PATENT DOCUMENTS

| | | |
|---|---|---|
| GB | 2 183 661 A | 6/1987 |
| WO | WO 89/06694 | 7/1989 |
| WO | WO 92/14843 | 9/1992 |

OTHER PUBLICATIONS

Breier et al. (1992) Development 114:521.
De Vries et al. (1992) Science 255:989.
Dvorak et al. (1991) J. Exp. Med. 174:1275.
Ellington and Szostak (1990) Abstract of papers presented at the 1990 meeting on RNA Processing, Cold Spring Harbor Laboratory, Cold Spring Harbor, NY, p. 84.
Ferrara et al. (1991) J. Cell. Biochem. 47:211.
Ferrara et al. (1992) Endocrine Rev. 13–18.
Folkman and Klagsbrun (1987) Science 235:442.
Galland et al. (1993) Oncogene 8:1233.
Gill and von Hippel (1989) Anal. Biochem. 182:319.
Gitay–Goren (1992) J. Biol. Chem. 267:6093.
Gutell et al. (1992) Nucl. Acids Research 20:5785.
Hobbs et al. (1973) Biochemistry 12:5138.
Jakeman et al. (1992) J. Clin. Invest. 89:244.
James et al. (1989) Meth. Enzymol. 180:227.
Joyce (1989) Gene 82:83.
Joyce and Inoue (1989) Nucleic Acids Research 17:711.
Kim et al. (1993) Nature 362:841.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Lowary and Uhlenbeck (1987) Nucleic Acids Research 15:10483.
Milligan et al. (1987) Nucleic Acids Research 15:8783.
Myoken et al. (1991) Proc. Natl. Acad. Sci. USA 88:5819.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Pepper et al. (1992) Biochem. Biophys. Res. Commun. 189:824.
Peretz et al. (1992) Biochem. Biophys. Res. Commun. 182:1340.
Plate et al. (1992) Nature 359:845.
Robertson and Joyce (1990) Nature 344:467.
Schneider et al. (1992) J. Mol. Biol. 228:862.
Senger et al. (1983) Science 219:983.
Shweiki et al. (1992) Nature 359:843.
Thiesen and Bach (1990) Nucleic Acids Research 18:3203.
Tuerk et al. (1990) J. Mol. Biol. 213:749.
Tuerk and Gold (1990) Science 249:505.
Unemori et al. (1992) J. Cell. Physiology 153:557.
Vaisman et al. (1990) J. Biol. Chem. 265:19461.
Yarus and Berg (1970) Anal. Biochem. 35:450.
Yeo et al. (1991) Biochem. Biophys. Res. Commun. 179:1568.
Szostak, "Structure and Activity of Ribozymes", in Redesigning the Molecules of Life, (S.A. Benner ed.) Springer–Verlag Berlin Heidelberg, pp. 87–113, (1988).

*Primary Examiner*—Stephanie W. Zitomer
(74) *Attorney, Agent, or Firm*—Swanson & Bratschun, LLC

(57) ABSTRACT

Methods are described for the identification and preparation of nucleic acid ligand ligands to vascular endothelial growth factor (VEGF). Included in the invention are specific RNA ligands to VEGF identified by the SELEX method.

9 Claims, 21 Drawing Sheets

Starting RNA:
5'-GGGAGCUCAGAAUAAACGCUCAA[-30N-]UUCGACAUGAGGCCCGGAUCCGGC-3'
(SEQ ID NO: 1)

PCR Primer 1:
5'-CCGAAGCTTAATACGACTCACTATAGGGAGCTCAGAATAAACGCTCAA-3'
          <u>Hind III</u>        <u>T7 Promoter</u>
(SEQ ID NO: 2)

PCR Primer 2:
5'-GCCGGATCCGGGCCTCATGTCGAA-3'
        <u>Bam H1</u>
(SEQ ID NO: 3)

FIGURE 1

| FAMILY 1 | | SEQ ID NO: |
|---|---|---|
| 1 | ucaaGAGUGAUGCU-CAUCCGCACUUGGUGACGUU | 4 |
| 3 (9) | caaUACCGGCAUGUC-CAUCGCUAGCGUAuucg | 5 |
| 5 (4) | aaUGCGUGUGACGCA-CAUCCGCACGCAuu | 6 |
| 7 | ucaaGGAGUGAUGCCCUAUCCGCACCUUGCCCA | 7 |
| 9 | ucaaGCUUGACNGCCCAUCCGAGCUUGAUCACGC | 8 |
| 46 | aaacgcucaaUCCUUGAUGCG-GAUCCGAGGAUGGGACGUUu | 9 |
| 50 | ACACCGUCGACCUAUGAUGCG-CAUCCGCACuucgac | 10 |
| 100 | aaCCGGUAGUCGCAUGGCCCAUCCGCCCGGuucgac | 11 |
| 107 | acgcucaaGUCAGCAUGGCCCACCGGCUUGACGUCUG | 12 |
| 112 | CACGGUUCGAUCUGUGACGUU-CAUCCGCACuucga | 13 |
| 119 | aacgcucaaGGAGCAGUGACGCA-CAUCCACACUCCAGCGuu | 14 |

| FAMILY 2 | | SEQ ID NO: |
|---|---|---|
| 24 (3) | UUCGAAUGCCGAGGCUC--GUGCCUUGACGGGuuc | 15 |
| 34 | UCGCGAAUGCCGACCACU---CAGGUUGAUGGGuucg | 16 |
| 102 | ucaaUCCGCCUGA---UCGGCUGAUGGGUUGACCG | 17 |
| 128 | GAAUGCCGAGCCCUAAGAGGCUUGAUGUGGuu | 18 |
| 27 | 5'-aaCCUUNAUGUGGCNCGAAC<br>UGCCGUGCCGAGGuu-3' | 19 |
| 44 | 5'-aaGCUUGAUGGGUUGACACAC<br>GUCAUGCCGAGCuu-3' | 20 |
| 55 | 5'-GUCGUCCUGCAUGGGCCGUAU<br>CGGUGCCGCG-3' | 21 |

FAMILY 3

```
                                                     SEQ ID NO:
         GCAGACGAAGGG-AACCUGGCGUCUCGGCACCuucg            22
12 (7)       AAGGAGG-ANCCUGCGUCUCGGCACUCCGCA            23
28        ucaaGGG-AACCUGCGUUCGGCACCUUGUUCCGU            24
75 (1)  aaAUGUGGGUUACCUGCGUUUCGGCACCACGUuu              25
137
         |....|....|....|....|....|....|....|....|
         1    5   10   15   20   25   30   35   40
```

FIGURE 2C

FAMILY 4

```
                                                              SEQ ID NO:
             CGACGGUAGAGUCUGUCCGUCAUCCCCA                        26
6         AAAGACCCCUGGUUGAGUCUGUCUGUCCCAGCCGuu                   27
35      GACCCAUCGUCAACGGUUGAGUCUGUCCGUuucgacaugagg               28
40          gcucaaGGUUGAGUCUGUCCCUUCGAGUAUCUGAUC                 29
56           UCGGACAGUUGGUUGAGUCUGUCCCAACUUuu                    30
90         GACCAUGUGACUGGUUGAGCCUGUCCCCAGuu                      31
106             AACGGUUGAGUCUGUCCGUAAGAGAGCGC                    32
138
         |....|....|....|....|....|....|....|....|
         1    5   10   15   20   25   30   35   40
```

FIGURE 2D

FAMILY 5

| | | SEQ ID NO: |
|---|---|---|
| 15 | UCGGAAUGUAGUUGACGUAUCCUUGU--CCGAuucgacau | 33 |
| 20 | aGGGUGUAGUUGGGACCUA--GUCCGCCGUACCuu | 34 |
| 21 | GGCAUAGUUGGACCUC--GUCCGCCGUGCCC | 35 |
| 84 | gcucaaUAGUUGGAGGCCUGUCCGCCGUAGAGCG | 36 |

FAMILY 6

| | | SEQ ID NO: |
|---|---|---|
| 25 | aGGGGUUCUA-GUGGAGACUCUGCCGCCCuu | 37 |
| 126 (2) | aACGGUUCUGUGGUGGACUA-GCCGGCCGuu | 38 |

Family 3 (SEQ ID NO: 44)

Family 2 (SEQ ID NO: 43)

Family 1 (SEQ ID NO: 42)

Family 6
(SEQ ID NO: 47)

Family 5
(SEQ ID NO: 46)

Family 4
(SEQ ID NO: 45)

SELEX Experiment A

Starting RNA:
5'-GGGAGACAAGAAUAACGCUCAA[-30N-]UUCGACAGGAGGC
UCACAACAGGC-3'                 (SEQ ID NO: 57)

PCR Primer 1:

5'-<u>TAATACGACTCACTATA</u>GGGAGACAAGAAUAACGCUCAA-3'
    T7 Promoter                            (SEQ ID NO: 58)

PCR Primer 2:

5'-GCCTGTTGTGAGCCTCCTGTCGAA-3'     (SEQ ID NO: 59)

SELEX Experiment B:

Starting RNA:
5'-GGGAGGACGAUGCGG[-50N-]CAGACGACTCGCCCGA-3'
                                                  (SEQ ID NO: 60)

PCR Primer 1:

5'-<u>TAATACGACTCACTATA</u>GGGAGGACGAUGCGG-3'
    T7 Promoter                             (SEQ ID NO: 61)

PCR Primer 2:

5'-TCGGGCGAGTCGTCTG-3'           (SEQ ID NO: 62)

FIGURE 8

| FAMILY 1 | | SEQ ID NO: |
|---|---|---|
| 14B | UGGCUGUGAUCAAUGCGGGGAGGUGAGGAAGGCCUUACAAAUCCUUCGG | 63 |
| 16B | UGUGAUCAAUGCGGUGCGGGGUAUGGGAUGGGAGUCUGGAAUGCUGGCU | 64 |
| 17B | CGCUGUGUUCAAUGGUCAAUGGGAUCGGCCGAGGAUGAACAAAUGGCGGGU | 65 |
| 25B | UGUUGAGCAAGCACUCAUGUGUCAAUGUGGGAGUGGAGCUGGAUGGGGGU | 66 |
| 28B | CAAGGGAGCGUUAGAGCCAUGUGGCAUGGGAUGAGGGUGGGAUUGGGGGU | 67 |
| 30B | CAUGGUUGUGAACUGUGUGAUCAAUGCGGGGAGGUAAUGGGUGGGGU | 68 |
| 33B | AUGAGUGACACAUGUCCAAUGCGGGUGUGGGUUGGGGGUAGCACGG | 69 |
| 34B | UGGGUCAAUGUGGUCAAUGUGGGAGGGCCUGGUACGGGUAGCACGG | 70 |
| 47B | CCGAGUGUGCUCAAUGUGUCAAUGCGGGGAGGGCAUCCGUACUGGUGUGGU | 71 |
| 46B | GUGCUCAGCAUUGUGUCAAUGCGGGGAGUUGGGUUGGCGACGG | 72 |
| CONSENSUS: | UGUGNUCAAUGNGGGG | 73 |

FIGURE 9A

| FAMILY 2 | | |
|---|---|---|
| 23B | CAUAGGCUUACAACAGAGCGGGGGUUCUGAUGGUAGACGCCGGACGCCC | 74 |
| 51B | UAUGAUGGUAGACGCCGUACCGCAUCAGGCCAAGU | |
| | CGUCACAGAUCGUG | |
| 14A | GCAACAGAGGCUGAUGGUAGACGCGCGCC-A | 75 |
| 17A | AGAGUCGCUGAUGGUAGACGCCGGCG-GAUC | 76 |
| 23A | GAGGCUGAUGGCAGACGCC-GGCC-GAAGACA | 77 |
| 24A | CCCUGAUGGUAGACGCCGGGGUGCCGGAA | 78 |
| | | 79 |
| CONSENSUS: | CUGAUGGUAGACGCCGG | 80 |

FIGURE 9B

```
FAMILY 3                                                                                              SEQ ID NO:
7B  CAGUGCUGAACUAAUCGAACGGGUCAAGGAGGGUCGAACGAGAUCGCCG                                                      81
26B              CACCUUCGUGGGUCAAGGAGGAGGGUCGCGAGGCCGCAGGAUCAACCGUGUG                                       82
54B                              GGUCAAGUUGGGUCGAGGAAGGCGCUCCCGAGUAUCGUAGUGUGCGACUGC                       83
8A                                   GAACUUGAUCGGGUCAAGGCGGGACGAA                                          84
15A                                        UGGGCGGACCAAGGAGGAGGGACGUGUAGGAAA                              85
16A                                 AAAAUGCACAAAUCGGGGUCAAGGAGGGACGA                                       86
45B                              AUGGGUUCGUGUGGUGAAUGGAGGAGGUUGGCUCGCAUGCUACUGUG                            87

CONSENSUS:                               GGUCAAGGNGGG                                                      88

FIGURE 9C

FAMILY 4                                                                                              SEQ ID NO:
43B    UGCACUAAGUCCGGUAGUGGGAGUGGUUGGGCCUGGAGUGCGC                                                         89
2A               AUCAAAGGUAGAGGGUGGCUGUGGCAAG                                                              90
9A               AAUCGAGGUAGCGGGCGGGUGGCUUGGCCAA                                                           91
60A              GCCUCGGAUCGGGCCAGCGGGUGGGAUGGCAA                                                          92
41A              AACGGAGUGUGGCGUUGGGUGCCAGGAA                                                              93

CONSENSUS:               GGUAGNGGGNG                                                                       94

FIGURE 9D

FAMILY 5                                                                                              SEQ ID NO:
44B    AAC---CG-AGUCGUGUGGGUUGGGCUCCAGUACAUCCCCGGUCUGGGUGU                                                 95
50B    UAACAUACGCAGUCGUGUGGGUAGGGAU-CACAAACUGCG---UAUCGUGU                                                 96

CONSENSUS:      AGUCGUGGGU-GGGG-U--CA                                                                      97

FIGURE 9E
```

| OTHER SEQUENCES | | SEQ ID NO: |
|---|---|---|
| 12A | AGUGUAGGAUAGGGGAUGGGAGGUCCGGGA | 98 |
| 20A | ACUGUGGGCUCUAGGGCAGUGGGAGUGGAG | 99 |
| 48A | AGUGGGACAGGAGGAUUGCGAGGUGAAGG | 100 |
| 11A | GUCAGGAGGACUGGAAGGUGGGACUGGUGA | 101 |
| 54A | GCAGGAGAGAGGGUGUUGGGUGCGGAUACA | 102 |
| 8B | AGGGUAGGAGGCUAAGCAUAGUUCAGAGGAGGUGGCGCGUGCCCCGUG | 103 |
| 32B | CAACAUUGGCACCAAUGCUCUGUGUUAAUGUGGGGUGGGAACGGCGCCG | 104 |
| 22B | ACCAAUGAUUGCAAUGAGGGCAGUGGGGAAUUGGGCUCGUGUGGU | 105 |
| 12B | GCAGUGGGUGAGGUCCGGGCACGAUUGAGUUUGAACGUCUGGCUUGGU | 106 |
| 53B | GUGUAGGUGUAGAGUGGAUGGCGGAGGUCCUAGUAGUUCUGUGCCUUGGU | 107 |
| 13B | CGCGGGAGAGGGUAGUGGGUGUGGAGGGGAAAUCUAGCCUCAGGGGUGGGGC | 108 |
| 1B | ACCCGCAUACGACCGCGGACUGCACGGGAAAUCUAGCCUCAGGGGUGGGGC | 109 |
| 5B | UGAAGAAGCGGGACUGCACGGGAUGGAGGACACGACUGCGCGGGGU | 110 |

FIGURE 9F

NITROCELLULOSE FILTER BINDERS:

| Clone | Sequence | SEQ ID NO: |
|---|---|---|
| 22A | ACACCAGGAGAGUGGGUUCGGGUGAGGACG | 111 |
| 33A | GUGGCUGAUGGCAGACGCCCGCUGCUGACG | 112 |
| 34A | UCGUGCCAGGACAUGGUGGCUCAUGGGUAA | 113 |
| 30A | AGGUACGGGGGAGGGAAGGAUAUAACGCGA | 114 |
| 32A | UGGAAAGGUGUGGAAAGAGGCAUCGGGGGG | 115 |
| 38A | UCAAUGGCAGGAAGAGAGGCAAGGAUGUGA | 116 |
| 45A | CAUGGGUAAGGGAGUGGGAGUGGUGAAUAG | 117 |
| 46A | GGAACGAGUAGGGCAGUGGGUGGUGAUGGC | 118 |
| 49A | UAGGGCAGAGGGAGUGGGUUAGGGCUGUGAU | 119 |
| 55A | GGGUAGUGGGAAGGGUAAGGGCCGAGGUGG | 120 |
| 19A | AAUACACACCCGGAAGGGUAGGGUUGAGGGAA | 121 |
| 59A | AGACUACACGCGCGGGUUAGGGUUGAGGGAA | 122 |
| 61A | UACGAGCAAGCGGGCGAAGGGUUGAGGGAA | 123 |
| 40A | CAAGGUGUGGAGGAGAUACGAUCUGCAG | 124 |
| 18A | GGAGGGAAGGAGGGCAGGUGAUGGGUCAG | 125 |
| 42A | UGAUGGCGGUAGUGGAGGUAAUGAGCGUGA | 126 |
| 1A  | GCAACUGGCGGGCGUAGUGGGUGUGAGGA | 127 |
| 4A  | GGAGGGCCUAUAGGGUGGUGUGUACGA | 128 |
| 36A | UAUAGGGGGCGUGAGGCGUAGGCAGGCGACA | 129 |
| 21A | GAGGGUUGGAGGCAUGGGCAGGAACCGG | 130 |
| 44A | CGUAGAACUGGCGGCAGUGGGGGAUGC | 131 |
| 13A | UGAGGCAGCGAGGGAUGUGGGGAGCGGGAC | 132 |
| 25A | CGAGGAUGGAGGCGUGUGAAGAUGCAA | 133 |
| 29A | GCAUCCGGGACAAGACGGUCGGUAAGGU | 134 |
| 47A | GUGUGCGGGUCAAGACGGGUGGCGUGG | 135 |
| 51A | UCAAACCAUGGCGGGUGUACGAGGAAC | 136 |
| 58A | CGAGUCCGAGGGAUGGUGGGUGUGCGGCAA | 137 |
| 10A | CAGUGUCGGAAGUACGAGAGGAGGUAUGAA | 138 |
| 2B  | CACCACUACGCGGGAAGGGUAGGGUUGGAGGUGGAGGACACAAAGCGCGUACCUGCCCC | 139 |
| 21B | UACGGUUAACGGGGUCUGGGUGUGGGUGUGGAGGGCAUGGGACCAAUACCGCGUG | 140 |
| 52B | AGGUCCUCGAGGGUCACGCGGGUGGAUGGAGGGUGGAAACACUAGAGCUUCGCCUG | 141 |
| 27B | AAACCCAUCCUGGGAUGGAGGUGGAGGUGGAAACACUAGAGCUUCGCCUG | 142 |
| 35B | AACUGGUGUCACGCGUUGAGGGUGGAGGUGGAUUCAACGGUCGAGGG | 143 |
| 38B | CAUGAAAGUAGGGUUAUGAAGGCCGUAGAUUCCGACGAUAGGGUUCCGC | 144 |
| 10B | GUCUAUUGGGUAGUGUUUCAAGAAUUCCGACGAUAGGGUAAAACAGUG | 145 |
| 19B | UGUAGGGAAGUACGAGAGUGGAGCGGCCGUAUAGGGUGGAGUGUGCU | 146 |

FIGURE 9G

SEQUENCE LISTING (1) GENERAL INFORMATION:

(iii) NUMBER OF SEQUENCES: 242

(2) INFORMATION FOR SEQ ID NO: 1:

(i) SEQUENCE CHARACTERISTICS:
       (A) LENGTH: 77 base pairs
       (B) TYPE: nucleic acid
       (C) STRANDEDNESS: single
       (D) TOPOLOGY: linear (xi) SEQUENCE DESCRIPTION: SEQ ID NO: 1:

GGGAGCUCAG AAUAAACGCU CAANNNNNNN NNNNNNNNNN NNNNNNNNNN        50

NNNUUCGACA UGAGGCCCGG AUCCGGC                                77

(2) INFORMATION FOR SEQ ID NO: 2:

(i) SEQUENCE CHARACTERISTICS:
       (A) LENGTH: 48 base pairs
       (B) TYPE: nucleic acid
       (C) STRANDEDNESS: single
       (D) TOPOLOGY: linear (xi) SEQUENCE DESCRIPTION: SEQ ID NO: 2:

CCGAAGCTTA ATACGACTCA CTATAGGGAG CTCAGAATAA ACGCTCAA         48

(2) INFORMATION FOR SEQ ID NO: 3:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO: 3:

GCCGGATCCG GGCCTCATGT CGAA                                   24

(2) INFORMATION FOR SEQ ID NO: 4:

(i) SEQUENCE CHARACTERISTICS:
       (A) LENGTH: 77 base pairs
       (B) TYPE: nucleic acid
       (C) STRANDEDNESS: single
       (D) TOPOLOGY: linear (xi) SEQUENCE DESCRIPTION: SEQ ID NO: 4:

GGGAGCUCAG AAUAAACGCU CAAGAGUGAU GCUCAUCCGC ACUUGGUGAC        50

GUUUUCGACA UGAGGCCCGG AUCCGGC                                77

(2) INFORMATION FOR SEQ ID NO: 5:

(i) SEQUENCE CHARACTERISTICS:
       (A) LENGTH: 77 base pairs
       (B) TYPE: nucleic acid
       (C) STRANDEDNESS: single
       (D) TOPOLOGY: linear (xi) SEQUENCE DESCRIPTION: SEQ ID NO: 5:

GGGAGCUCAG AAUAAACGCU CAAUACCGGC AUGCAUGUCC AUCGCUAGCG        50

GUAUUCGACA UGAGGCCCGG AUCCGGC                                77

(2) INFORMATION FOR SEQ ID NO: 6:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 6:

GGGAGCUCAG AAUAAACGCU CAAUGCGUGU UGUGACGCAC AUCCGCACGC      50

GCAUUCGACA UGAGGCCCGG AUCCGGC                              77

(2) INFORMATION FOR SEQ ID NO: 7:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 7:

GGGAGCUCAG AAUAAACGCU CAAGGAGUGA UGCCCUAUCC GCACCUUGGC      50

CCAUUCGACA UGAGGCCCGG AUCCGGC                              77

(2) INFORMATION FOR SEQ ID NO: 8:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 8:

GGGAGCUCAG AAUAAACGCU CAAGCUUGAC NGCCCAUCCG AGCUUGAUCA      50

CGCUUCGACA UGAGGCCCGG AUCCGGC                              77

(2) INFORMATION FOR SEQ ID NO: 9:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 9:

GGGAGCUCAG AAUAAACGCU CAAUCCUUGA UGCGGAUCCG AGGAUGGGAC      50

GUUUUCGACA UGAGGCCCGG AUCCGGC                              77

(2) INFORMATION FOR SEQ ID NO: 10:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 10:

GGGAGCUCAG AAUAAACGCU CAAACACCGU CGACCUAUGA UGCGCAUCCG      50

CACUUCGACA UGAGGCCCGG AUCCGGC                              77

(2) INFORMATION FOR SEQ ID NO: 11:

(i) SEQUENCE CHARACTERISTICS:
        (A) LENGTH: 76 base pairs (B) TYPE: nucleic acid
        (C) STRANDEDNESS: single
        (D) TOPOLOGY: linear (xi) SEQUENCE DESCRIPTION: SEQ ID NO: 11:

GGGAGCUCAG AAUAAACGCU CAACCGGUAG UCGCAUGGCC CAUCGCGCCC         50

GGUUCGACAU GAGGCCCGGA UCCGGC                                  76

(2) INFORMATION FOR SEQ ID NO: 12:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 12:

GGGAGCUCAG AAUAAACGCU CAAGUCAGCA UGGCCCACCG CGCUUGACGU         50

CUGUUCGACA UGAGGCCCGG AUCCGGC                                 77

(2) INFORMATION FOR SEQ ID NO: 13:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 13:

GGGAGCUCAG AAUAAACGCU CAACACGGUU CGAUCUGUGA CGUUCAUCCG         50

CACUUCGACA UGAGGCCCGG AUCCGGC                                 77

(2) INFORMATION FOR SEQ ID NO: 14:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 14:

GGGAGCUCAG AAUAAACGCU CAAGGAGCAG UGACGCACAU CCACACUCCA         50

GCGUUCGACA UGAGGCCCGG AUCCGGC                                 77

(2) INFORMATION FOR SEQ ID NO: 15:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 15:

GGGAGCUCAG AAUAAACGCU CAAUUCGAAU GCCGAGGCUC GUGCCUUGAC         50

GGGUUCGACA UGAGGCCCGG AUCCGGC                                 77

(2) INFORMATION FOR SEQ ID NO: 16:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 16:

GGGAGCUCAG AAUAAACGCU CAAUCGCGAA UGCCGACCAC UCAGGUUGAU        50

GGGUUCGACA UGAGGCCCGG AUCCGGC        77

(2) INFORMATION FOR SEQ ID NO: 17:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 17:

GGGAGCUCAG AAUAAACGCU CAAUGCCGGC CUGAUCGGCU GAUGGGUUGA        50

CCGUUCGACA UGAGGCCCGG AUCCGGC        77

(2) INFORMATION FOR SEQ ID NO: 18:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 18:

GGGAGCUCAG AAUAAACGCU CAAGAAUGCC GAGCCCUAAG AGGCUUGAUG        50

UGGUUCGACA UGAGGCCCGG AUCCGGC        77

(2) INFORMATION FOR SEQ ID NO: 19:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 19:

GGGAGCUCAG AAUAAACGCU CAACCUUNAU GUGGCNCGAA CUGCGUGCCG        50

AGGUUCGACA UGAGGCCCGG AUCCGGC        77

(2) INFORMATION FOR SEQ ID NO: 20:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 20:

GGGAGCUCAG AAUAAACGCU CAAGCUUGAU GGGUGACACA CGUCAUGCCG        50

AGCUUCGACA UGAGGCCCGG AUCCGGC        77

(2) INFORMATION FOR SEQ ID NO: 21:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 21:

GGGAGCUCAG AAUAAACGCU CAAGUCGUCC UGCAUGGGCC GUAUCGGUGC        50

```
GCGUUCGACA UGAGGCCCGG AUCCGGC                                          77

(2) INFORMATION FOR SEQ ID NO: 22:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 22:

GGGAGCUCAG AAUAAACGCU CAAGCAGACG AAGGGAACCU GCGUCUCGGC                  50

ACCUUCGACA UGAGGCCCGG AUCCGGC                                          77

(2) INFORMATION FOR SEQ ID NO: 23:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 23:

GGGAGCUCAG AAUAAACGCU CAAAAGGAGG ANCCUGCGUC UCGGCACUCC                  50

GCAUUCGACA UGAGGCCCGG AUCCGGC                                          77

(2) INFORMATION FOR SEQ ID NO: 24:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 24:

GGGAGCUCAG AAUAAACGCU CAAGGGAACC UGCGUUUCGG CACCUUGUUC                  50

CGUUUCGACA UGAGGCCCGG AUCCGGC                                          77

(2) INFORMATION FOR SEQ ID NO: 25:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO: 25:

GGGAGCUCAG AAUAAACGCU CAAAAAUGUG GGUUACCUGC GUUUCGGCAC                  50

CACGUUUCGA CAUGAGGCCC GGAUCCGGC                                        79

(2) INFORMATION FOR SEQ ID NO: 26:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 26:

GGGAGCUCAG AAUAAACGCU CAACGACGGU AGAGUCUGUC CCGUCAUCCC                  50

CCAUUCGACA UGAGGCCCGG AUCCGGC                                          77

(2) INFORMATION FOR SEQ ID NO: 27:
```

(i) SEQUENCE CHARACTERISTICS:
    (A) LENGTH: 77 base pairs
    (B) TYPE: nucleic acid
    (C) STRANDEDNESS: single
    (D) TOPOLOGY: linear (xi) SEQUENCE DESCRIPTION: SEQ ID NO: 27:

GGGAGCUCAG AAUAAACGCU CAAAAAGACC CCUGGUUGAG UCUGUCCCAG         50

CCGUUCGACA UGAGGCCCGG AUCCGGC                                  77

(2) INFORMATION FOR SEQ ID NO: 28:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 28:

GGGAGCUCAG AAUAAACGCU CAAGACCCAU CGUCAACGGU UGAGUCUGUC         50

CCGUUCGACA UGAGGCCCGG AUCCGGC                                  77

(2) INFORMATION FOR SEQ ID NO: 29:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 29:

GGGAGCUCAG AAUAAACGCU CAAGGUUGAG UCUGUCCCUU CGAGUAUCUG         50

AUCUUCGACA UGAGGCCCGG AUCCGGC                                  77

(2) INFORMATION FOR SEQ ID NO: 30:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 30:

GGGAGCUCAG AAUAAACGCU CAAUCGGACA GUUGGUUGAG UCUGUCCCAA         50

CUUUUCGACA UGAGGCCCGG AUCCGGC                                  77

(2) INFORMATION FOR SEQ ID NO: 31:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (xi) SEQUENCE DESCRIPTION: SEQ ID NO: 31:

GGGAGCUCAG AAUAAACGCU CAAGACCAUG UGACUGGUUG AGCCUGUCCC         50

AGUUCGACAU GAGGCCCGGA UCCGGC                                   76

(2) INFORMATION FOR SEQ ID NO: 32:

(i) SEQUENCE CHARACTERISTICS:
        (A) LENGTH: 77 base pairs
        (B) TYPE: nucleic acid (C) STRANDEDNESS: single
        (D) TOPOLOGY: linear (xi) SEQUENCE DESCRIPTION: SEQ ID NO: 32:

GGGAGCUCAG AAUAAACGCU CAAAACGGUU GAGUCUGUCC CGUAAGAGAG         50

CGCUUCGACA UGAGGCCCGG AUCCGGC                                  77

(2) INFORMATION FOR SEQ ID NO: 33:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 33:

GGGAGCUCAG AAUAAACGCU CAAUCGGAAU GUAGUUGACG UAUCCUUGUC         50

CGAUUCGACA UGAGGCCCGG AUCCGGC                                  77

(2) INFORMATION FOR SEQ ID NO: 34:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 34:

GGGAGCUCAG AAUAAACGCU CAAGGGUGUA GUUGGGACCU AGUCCGCCGU         50

ACCUUCGACA UGAGGCCCGG AUCCGGC                                  77

(2) INFORMATION FOR SEQ ID NO: 35:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 35:

GGGAGCUCAG AAUAAACGCU CAAGGCAUAG UUGGGACCUC GUCCGCCGUG         50

CCCUUCGACA UGAGGCCCGG AUCCGGC                                  77

(2) INFORMATION FOR SEQ ID NO: 36:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 36:

GGGAGCUCAG AAUAAACGCU CAAUAGUUGG AGGCCUGUCC UCGCCGUAGA         50

GCGUUCGACA UGAGGCCCGG AUCCGGC                                  77

(2) INFORMATION FOR SEQ ID NO: 37:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 37:

GGGAGCUCAG AAUAAACGCU CAAGGGGUUC UAGUGGAGAC UCUGCCGCGG          50

CCCUUCGACA UGAGGCCCGG AUCCGGC                                   77

(2) INFORMATION FOR SEQ ID NO: 38:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 38:

GGGAGCUCAG AAUAAACGCU CAAACGGUUC UGUGUGUGGA CUAGCCGCGG          50

CCGUUCGACA UGAGGCCCGG AUCCGGC                                   77

(2) INFORMATION FOR SEQ ID NO: 39:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 39:

GGGAGCUCAG AAUAAACGCU CAAGGGAUGU UUGGCUAUCU CGGAUAGUGC          50

CCCUUCGACA UGAGGCCCGG AUCCGGC                                   77

(2) INFORMATION FOR SEQ ID NO: 40:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 40:

GGGAGCUCAG AAUAAACGCU CAAGCUUAAU ACGACUCACU NUAGGGAGCU          50

CAGUUCGACA UGAGGCCCGG AUCCGGC                                   77

(2) INFORMATION FOR SEQ ID NO: 41:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 41:

GGGAGCUCAG AAUAAACGCU CAAUUGAGUG AUGUGCUUGA CGUAUCGCUG          50

CACUUCGACA UGAGGCCCGG AUCCGGC                                   77

(2) INFORMATION FOR SEQ ID NO: 42:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: RNA (ix) FEATURE:
        (A) NAME/KEY: N
        (B) LOCATION: 15

(D) OTHER INFORMATION: This symbol stands
                for the complimentary base for the N
                located in position 1

(xi) SEQUENCE DESCRIPTION: SEQ ID NO: 42:

NUGAUGVNCA UCCGN                                                              15

(2) INFORMATION FOR SEQ ID NO: 43:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: RNA (ix) FEATURE:
        (A) NAME/KEY: S
        (B) LOCATION: 11 and 12
        (D) OTHER INFORMATION: This symbol stands
            for the complimentary base for the S
            located in positions 9 and 10

(xi) SEQUENCE DESCRIPTION: SEQ ID NO: 43:

AAUGCCGASS SSUUGAUGGG UU                                                      22

(2) INFORMATION FOR SEQ ID NO: 44:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: RNA (ix) FEATURE:
        (A) NAME/KEY: H
        (B) LOCATION: 24
        (D) OTHER INFORMATION: This symbol stands
            for the complimentary base for the D
            located in position 2

(ix) FEATURE:
        (A) NAME/KEY: Y
        (B) LOCATION: 25
        (D) OTHER INFORMATION: This symbol stands
            for the complimentary base for the R
            located in position 25

(xi) SEQUENCE DESCRIPTION: SEQ ID NO: 44:

RDGGGAACCU GCGUYUCGGC ACCHY                                                   25

(2) INFORMATION FOR SEQ ID NO: 45:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: RNA (ix) FEATURE:
        (A) NAME/KEY: D
        (B) LOCATION: 18 and 19
        (D) OTHER INFORMATION: This symbol stands
            for the complimentary base for the H
            located in positions 1 and 2

(xi) SEQUENCE DESCRIPTION: SEQ ID NO: 45:

HHGGUUGAGU CUGUCCCDD    19

(2) INFORMATION FOR SEQ ID NO: 46:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: RNA (ix) FEATURE:
        (A) NAME/KEY: N
        (B) LOCATION: 18-20 and 27
        (D) OTHER INFORMATION: This symbol stands
            for the complimentary base for the N
            located in positions 1 and 10-12

(xi) SEQUENCE DESCRIPTION: SEQ ID NO: 46:

NRUAGUUGGN NNCUNSUNNN CGCCGUN    27

(2) INFORMATION FOR SEQ ID NO: 47:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: RNA (ix) FEATURE:
        (A) NAME/KEY: M
        (B) LOCATION: 20
        (D) OTHER INFORMATION: This symbol stands
            for the complimentary base for the K
            located in position 14

(ix) FEATURE:
        (A) NAME/KEY: S
        (B) LOCATION: 31
        (D) OTHER INFORMATION: This symbol stands
            for the complimentary base for the S
            located in position 2

(xi) SEQUENCE DESCRIPTION: SEQ ID NO: 47:

RSGGUUUCRU GUGKRGACUM UGCCGCGGCC SU    32

(2) INFORMATION FOR SEQ ID NO: 48:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 48:

GGGAACCUGC GUYUCGGCAC C    21

(2) INFORMATION FOR SEQ ID NO: 49:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 49:

GGUUGAGUCU GUCCC    15

(2) INFORMATION FOR SEQ ID NO: 50:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 50:

AAGCAGACGA AGGGAACCUG CGUCUCGGCA CCUUCGACAU    40

(2) INFORMATION FOR SEQ ID NO: 51:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 51:

GGCCGGUAGU CGCAUGGCCC AUCGCGCCCG G    31

(2) INFORMATION FOR SEQ ID NO: 52:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 52:

GGAAGCUUGA UGGGUGACAC ACGUCAUGCC GAGCU    35

(2) INFORMATION FOR SEQ ID NO: 53:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 53:

GGAAGGGAAC CUGCGUCUCG GCACCUUCG    29

(2) INFORMATION FOR SEQ ID NO: 54:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 54:

GGUCAACGGU UGAGUCUGUC CCGUUCGAC    29

(2) INFORMATION FOR SEQ ID NO: 55:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 55:

GGCUCAAUAG UUGGAGGCCU GUCCUCGCCG UAGAGC    36

(2) INFORMATION FOR SEQ ID NO: 56:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 56:

```
GGAACGGUUC UGUGUGUGGA CUAGCCGCGG CCGUU                    35
```

(2) INFORMATION FOR SEQ ID NO: 57:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 57:

```
GGGAGACAAG AAUAACGCUC AANNNNNNNN NNNNNNNNNN NNNNNNNNNN    50

NNUUCGACAG GAGGCUCACA ACAGGC                              76
```

(2) INFORMATION FOR SEQ ID NO: 58:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 58:

```
TAATACGACT CACTATAGGG AGACAAGAAU AACGCUCAA               39
```

(2) INFORMATION FOR SEQ ID NO: 59:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 59:

```
GCCTGTTGTG AGCCTCCTGT CGAA                               24
```

(2) INFORMATION FOR SEQ ID NO: 60:

(i) SEQUENCE CHARACTERISTICS:
        (A) LENGTH: 81 base pairs
        (B) TYPE: nucleic acid
        (C) STRANDEDNESS: single
        (D) TOPOLOGY: linear

```
    (ix) FEATURE:
         (D) OTHER INFORMATION: All C'S are 2'-NH2 cytosine (ix) FEATURE:
         (D) OTHER INFORMATION:  All U'S are 2'-NH2 uracil (xi) SEQUENCE DESCRIPTION: SEQ ID NO: 60:

GGGAGGACGA UGCGGNNNNN NNNNNNNNNN NNNNNNNNNN NNNNNNNNNN          50

NNNNNNNNNN NNNNNCAGAC GACTCGCCCG A                              81

(2) INFORMATION FOR SEQ ID NO: 61:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ix) FEATURE:
         (D) OTHER INFORMATION: All C'S are 2'-NH2 cytosine (ix) FEATURE:
         (D) OTHER INFORMATION:  All U'S are 2'-NH2 uracil (xi) SEQUENCE DESCRIPTION: SEQ ID NO: 61:

TAATACGACT CACTATAGGG AGGACGAUGC GG                             32

(2) INFORMATION FOR SEQ ID NO: 62:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ix) FEATURE:
         (D) OTHER INFORMATION: All C'S are 2'-NH2 cytosine (ix) FEATURE:
         (D) OTHER INFORMATION:  All U'S are 2'-NH2 uracil (xi) SEQUENCE DESCRIPTION: SEQ ID NO: 62:

TCGGGCGAGT CGTCTG                                               16

(2) INFORMATION FOR SEQ ID NO: 63:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
         (D) OTHER INFORMATION: All C'S are 2'-NH2 cytosine (ix) FEATURE:
         (D) OTHER INFORMATION:  All U'S are 2'-NH2 uracil (xi) SEQUENCE DESCRIPTION: SEQ ID NO: 63:

GGGAGGACGA UGCGGUGGCU GUGAUCAAUG CGGGGAGGUG AGGAAGGGCC          50

UUACAAAUCC UUCGGCAGAC GACTCGCCCG A                              81

(2) INFORMATION FOR SEQ ID NO: 64:

(i) SEQUENCE CHARACTERISTICS:
        (A) LENGTH: 81 base pairs
        (B) TYPE: nucleic acid
        (C) STRANDEDNESS: single
```

(D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 64:

GGGAGGACGA UGCGGUGUGA UCAAUGCGGU GGCGGGGUAU GGAUGGGAGU          50

CUGGAAUGCU GCGCUCAGAC GACTCGCCCG A                              81

(2) INFORMATION FOR SEQ ID NO: 65:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 65:

GGGAGGACGA UGCGGCGCUG UGUUCAAUGC GGGGAUCGGG CCGGAGGAUG          50

AACAAAUGGC GGGUCAGACG ACTCGCCCGA                                80

(2) INFORMATION FOR SEQ ID NO: 66:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 66:

GGGAGGACGA UGCGGUGUUG AGCAAGCACU CAUGUGGUCA AUGUGGGAGU          50

GGGAGCUGGU GGGGUCAGAC GACTCGCCCG A                              81

(2) INFORMATION FOR SEQ ID NO: 67:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 67:

GGGAGGACGA UGCGGCAAGG GAGCGUUAGA GCCAUGUGGU CAAUGAGGGG          50

UGGGAUUGGU UGGGUCAGAC GACTCGCCCG A                              81

(2) INFORMATION FOR SEQ ID NO: 68:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 68:

GGGAGGACGA UGCGGCAUGG UUGUGAACUG UUGUGAUCAA UGCGGGGAGG            50

GUAAUGGUGG GUGGUCAGAC GACTCGCCCG A                               81

(2) INFORMATION FOR SEQ ID NO: 69:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 69:

GGGAGGACGA UGCGGAUGAG UGACACAUGU GCUCAAUGCG GGGUGGGUUG            50

GUAGGGGUAG CACGGCAGAC GACTCGCCCG A                               81

(2) INFORMATION FOR SEQ ID NO: 70:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 70:

GGGAGGACGA UGCGGUGUGG UCAAUGUGGG GUAGGGCUGG UAGGGCAUUC            50

CGUACUGGUG UGGUCAGACG ACTCGCCCGA                                 80

(2) INFORMATION FOR SEQ ID NO: 71:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 71:

GGGAGGACGA UGCGGCCGAG UUGUGCUCAA UGUGGGGUCU GGGUACGGAC            50

GGGAACAGAU CUGGCAGACG ACTCGCCCGA                                           80

(2) INFORMATION FOR SEQ ID NO: 72:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 72:

GGGAGGACGA UGCGGGUGCU CAGCAUUGUG UGCUCAAUGC GGGGGAGUUU                     50

GGGUUGGCGA CGGCAGACGA CTCGCCCGA                                            79

(2) INFORMATION FOR SEQ ID NO: 73:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 73:

UGUGNUCAAU GNGGGG                                                          16

(2) INFORMATION FOR SEQ ID NO: 74:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 74:

GGGAGGACGA UGCGGCAUAG GCUUACAACA GAGCGGGGGU UCUGAUGGUA                     50

GACGCCGGGA CGCCCCAGAC GACTCGCCCG A                                         81

(2) INFORMATION FOR SEQ ID NO: 75:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 75:

GGGAGGACGA UGCGGUAUGA UGGUAGACGC CGUACCGCAU CAGGCCAAGU           50

CGUCACAGAU CGUGCAGACG ACTCGCCCGA                                80

(2) INFORMATION FOR SEQ ID NO: 76:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 76:

GGGAGACAAG AAUAACGCUC AAGCAACAGA GGCUGAUGGU AGACGCCGGC           50

CAUUCGACAG GAGGCUCACA ACAGGC                                    76

(2) INFORMATION FOR SEQ ID NO: 77:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 77:

GGGAGACAAG AAUAACGCUC AAAGAGUCGC UGAUGGUAGA CGCCGGCGGA           50

UCUUCGACAG GAGGCUCACA ACAGGC                                    76

(2) INFORMATION FOR SEQ ID NO: 78:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 78:

GGGAGACAAG AAUAACGCUC AAGAGGCUGA UGGCAGACGC GGCCGAAGAC           50

AUUCGACAGG AGGCUCACAA CAGGC                                     75

(2) INFORMATION FOR SEQ ID NO: 79:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ix) FEATURE:

(D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 79:

GGGAGACAAG AAUAACGCUC AACCCUGAUG GUAGACGCCG GGGUGCCGGA         50

AUUCGACAGG AGGCUCACAA CAGGC                                   75

(2) INFORMATION FOR SEQ ID NO: 80:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 80:

CUGAUGGUAG ACGCCGG                                            17

(2) INFORMATION FOR SEQ ID NO: 81:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 81:

GGGAGGACGA UGCGGCAGUG CUGAACUAAU CGAACGGGGU CAAGGAGGGU         50

CGAACGAGAU CUGCCGCAGA CGACTCGCCC GA                           82

(2) INFORMATION FOR SEQ ID NO: 82:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 82:

GGGAGGACGA UGCGGCACCU UCGUGGGGUC AAGGAGGGUC GCGAGGCCGC         50

AGGAUCAACC GUGUGCAGAC GACTCGCCCG A                            81

(2) INFORMATION FOR SEQ ID NO: 83:

(i) SEQUENCE CHARACTERISTICS:
        (A) LENGTH: 81 base pairs
        (B) TYPE: nucleic acid
        (C) STRANDEDNESS: single (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 83:

GGGAGGACGA UGCGGGGUCA AGUUGGGUCG AGGAAGCGCU CCCGAGUAUC          50

GUAGUGUGCG ACUGCCAGAC GACTCGCCCG A                             81

(2) INFORMATION FOR SEQ ID NO: 84:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 84:

GGGAGACAAG AAUAACGCUC AAGAACUUGA UCGGGGUCAA GGCGGGACGA          50

AUUCGACAGG AGGCUCACAA CAGGC                                    75

(2) INFORMATION FOR SEQ ID NO: 85:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 85:

GGGAGACAAG AAUAACGCUC AAUGGCGGGA CCAAGGAGGG ACGUGUAGGA          50

AAUUCGACAG GAGGCUCACA ACAGGC                                   76

(2) INFORMATION FOR SEQ ID NO: 86:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 86:

GGGAGACAAG AAUAACGCUC AAAAAAUGCA CAAAUCGGGG UCAAGGAGGG          50

ACGAUUCGAC AGGAGGCUCA CAACAGGC                                 78

(2) INFORMATION FOR SEQ ID NO: 87:

(i) SEQUENCE CHARACTERISTICS:
           (A) LENGTH: 78 base pairs
           (B) TYPE: nucleic acid
           (C) STRANDEDNESS: single
           (D) TOPOLOGY: linear (ix) FEATURE:
           (D) OTHER INFORMATION: All C'S are 2'-NH2 cytosine (ix) FEATURE:
           (D) OTHER INFORMATION:  All U'S are 2'-NH2 uracil (xi) SEQUENCE DESCRIPTION: SEQ ID NO: 87:

GGGAGGACGA UGCGGAUGGG UUCGUGUGGU GAAUGGAGGA GGUGGGCUCG          50

CAUGCUACUG UGCAGACGAC TCGCCCGA                                 78

(2) INFORMATION FOR SEQ ID NO: 88:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ix) FEATURE:
           (D) OTHER INFORMATION: All C'S are 2'-NH2 cytosine (ix) FEATURE:
           (D) OTHER INFORMATION:  All U'S are 2'-NH2 uracil (xi) SEQUENCE DESCRIPTION: SEQ ID NO: 88:

GGUCAAGGNG GG                                                  12

(2) INFORMATION FOR SEQ ID NO: 89:

(i) SEQUENCE CHARACTERISTICS:
           (A) LENGTH: 75 base pairs
           (B) TYPE: nucleic acid
           (C) STRANDEDNESS: single
           (D) TOPOLOGY: linear (ix) FEATURE:
           (D) OTHER INFORMATION: All C'S are 2'-NH2 cytosine (ix) FEATURE:
           (D) OTHER INFORMATION:  All U'S are 2'-NH2 uracil (xi) SEQUENCE DESCRIPTION: SEQ ID NO: 89:

GGGAGGACGA UGCGGUGCAC UAAGUCCGGG UAGUGGGAGU GGUUGGGCCU          50

GGAGUGCGCC AGACGACTCG CCCGA                                    75

(2) INFORMATION FOR SEQ ID NO: 90:

(i) SEQUENCE CHARACTERISTICS:
           (A) LENGTH: 76 base pairs
           (B) TYPE: nucleic acid
           (C) STRANDEDNESS: single
           (D) TOPOLOGY: linear (ix) FEATURE:
           (D) OTHER INFORMATION: All C'S are 2'-NH2 cytosine (ix) FEATURE:
           (D) OTHER INFORMATION:  All U'S are 2'-NH2 uracil (xi) SEQUENCE DESCRIPTION: SEQ ID NO: 90:

GGGAGACAAG AAUAACGCUC AAAUCAAAGG GUAGAGGGUG GGCUGUGGCA          50

AGUUCGACAG GAGGCUCACA ACAGGC                                   76

(2) INFORMATION FOR SEQ ID NO: 91:

(i) SEQUENCE CHARACTERISTICS:
      (A) LENGTH: 76 base pairs
      (B) TYPE: nucleic acid
      (C) STRANDEDNESS: single
      (D) TOPOLOGY: linear (ix) FEATURE:
      (D) OTHER INFORMATION: All C'S are 2'-NH2 cytosine (ix) FEATURE:
      (D) OTHER INFORMATION:  All U'S are 2'-NH2 uracil (xi) SEQUENCE DESCRIPTION: SEQ ID NO: 91:

GGGAGACAAG AAUAACGCUC AAAAUCGAGG GUAGCGGGCG CGGCUUGGCC         50

AAUUCGACAG GAGGCUCACA ACAGGC                                  76

(2) INFORMATION FOR SEQ ID NO: 92:

(i) SEQUENCE CHARACTERISTICS:
      (A) LENGTH: 77 base pairs
      (B) TYPE: nucleic acid
      (C) STRANDEDNESS: single
      (D) TOPOLOGY: linear (ix) FEATURE:
      (D) OTHER INFORMATION: All C'S are 2'-NH2 cytosine (ix) FEATURE:
      (D) OTHER INFORMATION:  All U'S are 2'-NH2 uracil (xi) SEQUENCE DESCRIPTION: SEQ ID NO: 92:

GGGAGACAAG AAUAACGCUC AAGCCUCGGA UCGGGCAGCG GGUGGGAUGG         50

CAAUUCGACA GGAGGCUCAC AACAGGC                                 77

(2) INFORMATION FOR SEQ ID NO: 93:

(i) SEQUENCE CHARACTERISTICS:
      (A) LENGTH: 76 base pairs
      (B) TYPE: nucleic acid
      (C) STRANDEDNESS: single
      (D) TOPOLOGY: linear (ix) FEATURE:
      (D) OTHER INFORMATION: All C'S are 2'-NH2 cytosine (ix) FEATURE:
      (D) OTHER INFORMATION:  All U'S are 2'-NH2 uracil (xi) SEQUENCE DESCRIPTION: SEQ ID NO: 93:

GGGAGACAAG AAUAACGCUC AAAACGGAGU GGUAGGCGUU GGGUGCCAGG         50

AAUUCGACAG GAGGCUCACA ACAGGC                                  76

(2) INFORMATION FOR SEQ ID NO: 94:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ix) FEATURE:
      (D) OTHER INFORMATION: All C'S are 2'-NH2 cytosine (ix) FEATURE:
      (D) OTHER INFORMATION:  All U'S are 2'-NH2 uracil (xi) SEQUENCE DESCRIPTION: SEQ ID NO: 94:

GGUAGNGGGN G                                                          11

(2) INFORMATION FOR SEQ ID NO: 95:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 95:

GGGAGGACGA UGCGGAACCG AGUCGUGUGG GUUGGGGCUC CAGUACAUCC                 50

CCGGUCUGGG UGUCAGACGA CTCGCCCGA                                       79

(2) INFORMATION FOR SEQ ID NO: 96:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 96:

GGGAGGACGA UGCGGUAACA UACGCAGUCG UGUGGGUAGG GGAUCACAAA                 50

CUGCGUAUCG UGUCAGACGA CTCGCCCGA                                       79

(2) INFORMATION FOR SEQ ID NO: 97:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 97:

GGGAGACAAG AAUAACGCUC AAAGUCGUGU GGGUGGGGUC AUUCGACAGG                 50

AGGCUCACAA CAGGC                                                      65

(2) INFORMATION FOR SEQ ID NO: 98:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 98:

GGGAGACAAG AAUAACGCUC AAAGUGUAGG AUAGGGGAUG GGAGGUCCGG          50

GAUUCGACAG GAGGCUCACA ACAGGC                                   76

(2) INFORMATION FOR SEQ ID NO: 99:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 99:

GGGAGACAAG AAUAACGCUC AAACUGUGGG CUCUAGGGCA GUGGGAGUGG          50

AGUUCGACAG GAGGCUCACA ACAGGC                                   76

(2) INFORMATION FOR SEQ ID NO: 100:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 100:

GGGAGACAAG AAUAACGCUC AAAGUGGGAC AGGGAUUGCG GAGGGUGGAA          50

GGUUCGACAG GAGGCUCACA ACAGGC                                   76

(2) INFORMATION FOR SEQ ID NO: 101:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 101:

GGGAGACAAG AAUAACGCUC AAGUCAGGAG GACUGGAAGG UGGGACUGGU          50

GAUUCGACAG GAGGCUCACA ACAGGC                                   76

(2) INFORMATION FOR SEQ ID NO: 102:

(i) SEQUENCE CHARACTERISTICS:
        (A) LENGTH: 76 base pairs
        (B) TYPE: nucleic acid
        (C) STRANDEDNESS: single (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 102:

GGGAGACAAG AAUAACGCUC AAGCAGGAGA GAGGGUGUUG GGUGCGGAUA          50

CAUUCGACAG GAGGCUCACA ACAGGC                                   76

(2) INFORMATION FOR SEQ ID NO: 103:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 103:

GGGAGGACGA UGCGGAGGGU AGGAGGCUAA GCAUAGUUCA GAGGAGGUGG          50

CGCGUGCCCC CGUGCAGACG ACTCGCCCGA                               80

(2) INFORMATION FOR SEQ ID NO: 104:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 104:

GGGAGGACGA UGCGGCAACA UUGGCACCAA UGCUCUGUGU UAAUGUGGGG          50

UGGGAACGGC GCCGCAGACG ACTCGCCCGA                               80

(2) INFORMATION FOR SEQ ID NO: 105:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 105:

GGGAGGACGA UGCGGACCAA UGAUUGCAAU GAGGGCAGUG GGGGGGAAUU          50

GGGCUCGUGU GGUCAGACGA CTCGCCCGA                                79

(2) INFORMATION FOR SEQ ID NO: 106:

(i) SEQUENCE CHARACTERISTICS:
    (A) LENGTH: 81 base pairs
    (B) TYPE: nucleic acid
    (C) STRANDEDNESS: single
    (D) TOPOLOGY: linear (ix) FEATURE:
    (D) OTHER INFORMATION: All C'S are 2'-NH2 cytosine (ix) FEATURE:
    (D) OTHER INFORMATION: All U'S are 2'-NH2 uracil (xi) SEQUENCE DESCRIPTION: SEQ ID NO: 106:

GGGAGGACGA UGCGGGCAGU GGGUGAGGUC CGGGCACGAU UGAGUUUGAA          50

CGGUUCUGGC UUGGUCAGAC GACTCGCCCG A                              81

(2) INFORMATION FOR SEQ ID NO: 107:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 107:

GGGAGGACGA UGCGGGUGGU AGGUGUAGAG UGGAUGGCGG AGGUCCUAGU          50

AGUUCUGUGC CUGGUCAGAC GACTCGCCCG A                              81

(2) INFORMATION FOR SEQ ID NO: 108:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 108:

GGGAGGACGA UGCGGCGCGG GAGAGGGUAG UGGGUGUGGU GCUUGGACAA          50

GCAGCGCAGA CGACTCGCCC GA                                        72

(2) INFORMATION FOR SEQ ID NO: 109:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 109:

GGGAGGACGA UGCGGACCCG CAUACGGACC GCGGAGGGGG AAAUCUAGCC          50

UCAGGGGUGG CGGGCCAGAC GACUCGCCCG A                                81

(2) INFORMATION FOR SEQ ID NO: 110:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 110:

GGGAGGACGA UGCGGUGAAG AAGCGGGGAC UGCACGACGG GAUGGAGGGA            50

CACGACUGCG GGGUCAGACG ACUCGCCCGA                                  80

(2) INFORMATION FOR SEQ ID NO: 111:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 111:

GGGAGACAAG AAUAACGCUC AAACACCAGG AGAGUGGGUU CGGGUGAGGA            50

CGUUCGACAG GAGGCUCACA ACAGGC                                      76

(2) INFORMATION FOR SEQ ID NO: 112:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 112:

GGGAGACAAG AAUAACGCUC AAGUGGCUGA UGGCAGACGC CGGCUGCUGA            50

CGUUCGACAG GAGGCUCACA ACAGGC                                      76

(2) INFORMATION FOR SEQ ID NO: 113:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:

(D) OTHER INFORMATION: All U'S are 2'-NH2 uracil (xi) SEQUENCE DESCRIPTION: SEQ ID NO: 113:

GGGAGACAAG AAUAACGCUC AAUCGUGCCA GGACAUGGUG GCUCAUGGGU          50

AAUUCGACAG GAGGCUCACA ACAGGC                                   76

(2) INFORMATION FOR SEQ ID NO: 114:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 114:

GGGAGACAAG AAUAACGCUC AAAGGUACGG GGGAGGGAAG GAUAUAACGC          50

GAUUCGACAG GAGGCUCACA ACAGGC                                   76

(2) INFORMATION FOR SEQ ID NO: 115:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 115:

GGGAGACAAG AAUAACGCUC AAUGGAAAGG UGUGGAAAGA GGCAUCGGGG          50

GGUUCGACAG GAGGCUCACA ACAGGC                                   76

(2) INFORMATION FOR SEQ ID NO: 116:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 116:

GGGAGACAAG AAUAACGCUC AAUCAAUGGG CAGGAAGAGG GAAGGGAUGU          50

GAUUCGACAG GAGGCUCACA ACAGGC                                   76

(2) INFORMATION FOR SEQ ID NO: 117:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
    (D) OTHER INFORMATION: All C'S are 2'-NH2 cytosine (ix) FEATURE:
    (D) OTHER INFORMATION: All U'S are 2'-NH2 uracil (xi) SEQUENCE DESCRIPTION: SEQ ID NO: 117:

GGGAGACAAG AAUAACGCUC AACAUGGGUA AGGGAGUGGG AGUGGUGAAU           50

AGUUCGACAG GAGGCUCACA ACAGGC                                    76

(2) INFORMATION FOR SEQ ID NO: 118:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
    (D) OTHER INFORMATION: All C'S are 2'-NH2 cytosine (ix) FEATURE:
    (D) OTHER INFORMATION: All U'S are 2'-NH2 uracil (xi) SEQUENCE DESCRIPTION: SEQ ID NO: 118:

GGGAGACAAG AAUAACGCUC AAGGAACGAG UAGGGCAGUG GGUGGUGAUG           50

GCUUCGACAG GAGGCUCACA ACAGGC                                    76

(2) INFORMATION FOR SEQ ID NO: 119:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
    (D) OTHER INFORMATION: All C'S are 2'-NH2 cytosine (ix) FEATURE:
    (D) OTHER INFORMATION: All U'S are 2'-NH2 uracil (xi) SEQUENCE DESCRIPTION: SEQ ID NO: 119:

GGGAGACAAG AAUAACGCUC AAUAGGGCAG AGGGAGUGGU UAGGGCUGUG           50

AUUUCGACAG GAGGCUCACA ACAGGC                                    76

(2) INFORMATION FOR SEQ ID NO: 120:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
    (D) OTHER INFORMATION: All C'S are 2'-NH2 cytosine (ix) FEATURE:
    (D) OTHER INFORMATION: All U'S are 2'-NH2 uracil (xi) SEQUENCE DESCRIPTION: SEQ ID NO: 120:

GGGAGACAAG AAUAACGCUC AAGGGUAGUG GGAAGGGUAA GGGCCGAGGU           50

GGUUCGACAG GAGGCUCACA ACAGGC                                    76

(2) INFORMATION FOR SEQ ID NO: 121:

```
    (i) SEQUENCE CHARACTERISTICS:
         (A) LENGTH: 76 base pairs
         (B) TYPE: nucleic acid
         (C) STRANDEDNESS: single
         (D) TOPOLOGY: linear (ix) FEATURE:
         (D) OTHER INFORMATION: All C'S are 2'-NH2 cytosine (ix) FEATURE:
         (D) OTHER INFORMATION:  All U'S are 2'-NH2 uracil (xi) SEQUENCE DESCRIPTION: SEQ ID NO: 121:

GGGAGACAAG AAUAACGCUC AAAAUACACA CCGCGGGAAG GGAGGGUGGA          50

AAUUCGACAG GAGGCUCACA ACAGGC                                   76

(2) INFORMATION FOR SEQ ID NO: 122:

(i) SEQUENCE CHARACTERISTICS:
         (A) LENGTH: 76 base pairs
         (B) TYPE: nucleic acid
         (C) STRANDEDNESS: single
         (D) TOPOLOGY: linear (ix) FEATURE:
         (D) OTHER INFORMATION: All C'S are 2'-NH2 cytosine (ix) FEATURE:
         (D) OTHER INFORMATION:  All U'S are 2'-NH2 uracil (xi) SEQUENCE DESCRIPTION: SEQ ID NO: 122:

GGGAGACAAG AAUAACGCUC AAAGACUACA GCGCGGGUUA GGGUUGAGGG          50

AAUUCGACAG GAGGCUCACA ACAGGC                                   76

(2) INFORMATION FOR SEQ ID NO: 123:

(i) SEQUENCE CHARACTERISTICS:
         (A) LENGTH: 76 base pairs
         (B) TYPE: nucleic acid
         (C) STRANDEDNESS: single
         (D) TOPOLOGY: linear (ix) FEATURE:
         (D) OTHER INFORMATION: All C'S are 2'-NH2 cytosine (ix) FEATURE:
         (D) OTHER INFORMATION:  All U'S are 2'-NH2 uracil (xi) SEQUENCE DESCRIPTION: SEQ ID NO: 123:

GGGAGACAAG AAUAACGCUC AAUACGAGCA AGCGGGCGAA GGGUUGAGGG          50

AAUUCGACAG GAGGCUCACA ACAGGC                                   76

(2) INFORMATION FOR SEQ ID NO: 124:

(i) SEQUENCE CHARACTERISTICS:
         (A) LENGTH: 76 base pairs
         (B) TYPE: nucleic acid
         (C) STRANDEDNESS: single
         (D) TOPOLOGY: linear (ix) FEATURE:
         (D) OTHER INFORMATION: All C'S are 2'-NH2 cytosine (ix) FEATURE:
         (D) OTHER INFORMATION:  All U'S are 2'-NH2 uracil (xi) SEQUENCE DESCRIPTION: SEQ ID NO: 124:

GGGAGACAAG AAUAACGCUC AACAAGGUGG UGGAGGAGGA UACGAUCUGC          50
```

```
AGUUCGACAG GAGGCUCACA ACAGGC                                                  76

(2) INFORMATION FOR SEQ ID NO: 125:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 125:

GGGAGACAAG AAUAACGCUC AAGGAGGGAA GGAGGGCAGG UGAUGGGUCA                         50

GUUCGACAGG AGGCUCACAA CAGGC                                                   75

(2) INFORMATION FOR SEQ ID NO: 126:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 126:

GGGAGACAAG AAUAACGCUC AAUGAUGGCG GUAGUGGAGG UAAUGAGCGU                         50

GAUUCGACAG GAGGCUCACA ACAGGC                                                  76

(2) INFORMATION FOR SEQ ID NO: 127:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 127:

GGGAGACAAG AAUAACGCUC AAGCAACUGG GGGCGGGUGG UGUGAGGAUU                         50

CGACAGGAGG CUCACAACAG GC                                                      72

(2) INFORMATION FOR SEQ ID NO: 128:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil
```

(xi) SEQUENCE DESCRIPTION: SEQ ID NO: 128:

GGGAGACAAG AAUAACGCUC AAGGAGGGGC CUAUAGGGGU GGUGGUGUAC          50

GAUUCGACAG GAGGCUCACA ACAGGC                                   76

(2) INFORMATION FOR SEQ ID NO: 129:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 129:

GGGAGACAAG AAUAACGCUC AAUAUAGGGU AGUGGGUGUA GGUAGGGCGA          50

CAUUCGACAG GAGGCUCACA ACAGGC                                   76

(2) INFORMATION FOR SEQ ID NO: 130:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 130:

GGGAGACAAG AAUAACGCUC AAGAGGGUUG GAGGGCAUGG GGCAGGAACC          50

GGUUCGACAG GAGGCUCACA ACAGGC                                   76

(2) INFORMATION FOR SEQ ID NO: 131:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 131:

GGGAGACAAG AAUAACGCUC AACGUAGAAC UGGCGGGCAG UGGGGGGAU           50

GCUUCGACAG GAGGCUCACA ACAGGC                                   76

(2) INFORMATION FOR SEQ ID NO: 132:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
              (D) OTHER INFORMATION: All C'S are 2'-NH2 cytosine (ix) FEATURE:
              (D) OTHER INFORMATION:  All U'S are 2'-NH2 uracil (xi) SEQUENCE DESCRIPTION: SEQ ID NO: 132:

GGGAGACAAG AAUAACGCUC AAUGAGGGA CGAGGGAUGU GGGGAGCGGG            50

ACUUCGACAG GAGGCUCACA ACAGGC                                    76

(2) INFORMATION FOR SEQ ID NO: 133:

(i) SEQUENCE CHARACTERISTICS:
              (A) LENGTH: 76 base pairs
              (B) TYPE: nucleic acid
              (C) STRANDEDNESS: single
              (D) TOPOLOGY: linear (ix) FEATURE:
              (D) OTHER INFORMATION: All C'S are 2'-NH2 cytosine (ix) FEATURE:
              (D) OTHER INFORMATION:  All U'S are 2'-NH2 uracil (xi) SEQUENCE DESCRIPTION: SEQ ID NO: 133:

GGGAGACAAG AAUAACGCUC AACGAGGGAU GGGAGGCGUG UGGAAGAUGC           50

AAUUCGACAG GAGGCUCACA ACAGGC                                    76

(2) INFORMATION FOR SEQ ID NO: 134:

(i) SEQUENCE CHARACTERISTICS:
              (A) LENGTH: 76 base pairs
              (B) TYPE: nucleic acid
              (C) STRANDEDNESS: single
              (D) TOPOLOGY: linear (ix) FEATURE:
              (D) OTHER INFORMATION: All C'S are 2'-NH2 cytosine (ix) FEATURE:
              (D) OTHER INFORMATION:  All U'S are 2'-NH2 uracil (xi) SEQUENCE DESCRIPTION: SEQ ID NO: 134:

GGGAGACAAG AAUAACGCUC AAGCAUCCGG GGACAAGAUG GGUCGGUAAG           50

GUUUCGACAG GAGGCUCACA ACAGGC                                    76

(2) INFORMATION FOR SEQ ID NO: 135:

(i) SEQUENCE CHARACTERISTICS:
              (A) LENGTH: 75 base pairs
              (B) TYPE: nucleic acid
              (C) STRANDEDNESS: single
              (D) TOPOLOGY: linear (ix) FEATURE:
              (D) OTHER INFORMATION: All C'S are 2'-NH2 cytosine (ix) FEATURE:
              (D) OTHER INFORMATION:  All U'S are 2'-NH2 uracil (xi) SEQUENCE DESCRIPTION: SEQ ID NO: 135:

GGGAGACAAG AAUAACGCUC AAGUGUGCGG GGUCAAGACG GGUGGCGUGC           50

GUUCGACAGG AGGCUCACAA CAGGC                                     75

(2) INFORMATION FOR SEQ ID NO: 136:

(i) SEQUENCE CHARACTERISTICS:

(A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 136:

GGGAGACAAG AAUAACGCUC AAUCAAACCA UGGGGCGGGU GGUACGAGGA         50

ACUUCGACAG GAGGCUCACA ACAGGC                                   76

(2) INFORMATION FOR SEQ ID NO: 137:
    (i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 137:

GGGAGACAAG AAUAACGCUC AACGAGUCCG AGGGAUGGGU GGUGUGCGGC         50

AAUUCGACAG GAGGCUCACA ACAGGC                                   76

(2) INFORMATION FOR SEQ ID NO: 138:
    (i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 138:

GGGAGACAAG AAUAACGCUC AACAGUGUCG GAGAGGAGGA UGGAGGUAUG         50

AAUUCGACAG GAGGCUCACA ACAGGC                                   76

(2) INFORMATION FOR SEQ ID NO: 139:
    (i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO: 139:

GGGAGGACGA UGCGGCACCA CUACGCGGGA AGGGUAGGGU GGAUUACAAG         50

GUGUGACCGC UCCGUCAGAC GACTCGCCCG A                             81

(2) INFORMATION FOR SEQ ID NO: 140:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 140:

GGGAGGACGA UGCGGUACGG UUAACGGGGG UGGUGUGGGA GGACACAAAG         50

CGCGUACCUG CCCCCAGACG ACTCGCCCGA                              80

(2) INFORMATION FOR SEQ ID NO: 141:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 141:

GGGAGGACGA UGCGGAGGUC CUCGAGGGUC UGGGUGUGGG AGUGGGCAUG         50

GACCAAUACC GCGUGCAGAC GACTCGCCCG A                            81

(2) INFORMATION FOR SEQ ID NO: 142:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 142:

GGGAGGACGA UGCGGAAACC CAUCCUGCGC GGGAUGGGAG GGUGGAAACA         50

CUAGAGCUUC GCCUGCAGAC GACTCGCCCG A                            81

(2) INFORMATION FOR SEQ ID NO: 143:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION:  All U'S are 2'-NH2 uracil (xi) SEQUENCE DESCRIPTION: SEQ ID NO: 143:

GGGAGGACGA UGCGGAACUG GUGGUCACGC GUUGAGGUGG UGGAGGUGGA          50

UUCAACGGUC GAGGGCAGAC GACTCGCCCG A                             81

(2) INFORMATION FOR SEQ ID NO: 144:

(i) SEQUENCE CHARACTERISTICS:
            (A) LENGTH: 81 base pairs
            (B) TYPE: nucleic acid
            (C) STRANDEDNESS: single
            (D) TOPOLOGY: linear (ix) FEATURE:
            (D) OTHER INFORMATION: All C'S are 2'-NH2 cytosine (ix) FEATURE:
            (D) OTHER INFORMATION:  All U'S are 2'-NH2 uracil (xi) SEQUENCE DESCRIPTION: SEQ ID NO: 144:

GGGAGGACGA UGCGGCAUGA AAGUAGGGUU AUGAAGGCGG UAGAUGGAGG          50

AGGUUGGGUU GCCGCCAGAC GACTCGCCCG A                             81

(2) INFORMATION FOR SEQ ID NO: 145:

(i) SEQUENCE CHARACTERISTICS:
            (A) LENGTH: 81 base pairs
            (B) TYPE: nucleic acid
            (C) STRANDEDNESS: single
            (D) TOPOLOGY: linear (ix) FEATURE:
            (D) OTHER INFORMATION: All C'S are 2'-NH2 cytosine (ix) FEATURE:
            (D) OTHER INFORMATION:  All U'S are 2'-NH2 uracil (xi) SEQUENCE DESCRIPTION: SEQ ID NO: 145:

GGGAGGACGA UGCGGGUCUA UUGGGUAGGU GUUUGCAAGA AUUCCGCACG          50

AUAGGUAAAA CAGUGCAGAC GACTCGCCCG A                             81

(2) INFORMATION FOR SEQ ID NO: 146:

(i) SEQUENCE CHARACTERISTICS:
            (A) LENGTH: 80 base pairs
            (B) TYPE: nucleic acid
            (C) STRANDEDNESS: single
            (D) TOPOLOGY: linear (ix) FEATURE:
            (D) OTHER INFORMATION: All C'S are 2'-NH2 cytosine (ix) FEATURE:
            (D) OTHER INFORMATION:  All U'S are 2'-NH2 uracil (xi) SEQUENCE DESCRIPTION: SEQ ID NO: 146:

GGGAGGACGA UGCGGUGUAG GGGAAGUACG AGAGUGGGAG CGGCCGUAUA          50

GGUGGGAGUG UGCUCAGACG ACTCGCCCGA                               80

(2) INFORMATION FOR SEQ ID NO: 147:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ix) FEATURE:

(A) NAME/KEY: modified base
            (B) LOCATION: 2..4, 15, 17..18
            (D) OTHER INFORMATION:  C at positions 2-4, 15, 17-18
                are 2'NH2 cytosine (ix) FEATURE:
            (A) NAME/KEY: modified base
            (B) LOCATION: 5, 8, 11, 23
            (D) OTHER INFORMATION: U at positions 5, 8, 11, 23 are
                2'NH2 uracil (xi) SEQUENCE DESCRIPTION: SEQ ID NO: 147:

ACCCUGAUGG UAGACGCCGG GGUG                                          24

(2) INFORMATION FOR SEQ ID NO: 148:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ix) FEATURE:
            (A) NAME/KEY: modified base
            (B) LOCATION: 2..4, 15, 17..18
            (D) OTHER INFORMATION: C at positions 2-4, 15, 17-18 are
                2'NH2 cytosine (ix) FEATURE:
            (A) NAME/KEY: modified base
            (B) LOCATION: 5, 8, 11, 23
            (D) OTHER INFORMATION: U at positions 5, 8, 11 and 23
                are 2'NH2 uracil (ix) FEATURE:
            (A) NAME/KEY: modified base
            (B) LOCATION: 12, 14
            (D) OTHER INFORMATION: A at positions 12 and 14 are
                2'OMe adenosine (ix) FEATURE:
            (A) NAME/KEY: modified base
            (B) LOCATION: 13, 16, 19..21, 22, 24
            (D) OTHER INFORMATION: G at positions 13, 16, 19-21, 22
                and 24 are 2'OMe guanosine (xi) SEQUENCE DESCRIPTION: SEQ ID NO: 148:

ACCCUGAUGG UAGACGCCGG GGUG                                          24

(2) INFORMATION FOR SEQ ID NO: 149:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ix) FEATURE:
            (A) NAME/KEY: modified base
            (B) LOCATION: 6..8, 19, 21..22
            (D) OTHER INFORMATION:  C at positions 6-8, 19 and 21-22
                are 2'NH2 cytosine (ix) FEATURE:
            (A) NAME/KEY: modified base
            (B) LOCATION: 9, 12, 15, 27
            (D) OTHER INFORMATION: U at positions 9, 12, 15 and 27
                are 2'NH2 uracil (ix) FEATURE:
            (A) NAME/KEY: modified base
            (B) LOCATION: 1..4, 29..33
            (D) OTHER INFORMATION: T at positions 1-4 and 29-33 are
                2' deoxy phosphorothioate thymidine (xi) SEQUENCE DESCRIPTION: SEQ ID NO: 149:

TTTTACCCUG AUGGUAGACG CCGGGGUGTT TTT                33

(2) INFORMATION FOR SEQ ID NO: 150:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (D) OTHER INFORMATION: All A's, C's, G's, T's are 2'
            deoxy-nucleotide derivatives (ix) FEATURE:
        (A) NAME/KEY: modified base
        (B) LOCATION: 1..4, 29..33
        (D) OTHER INFORMATION: T at positions 1-4 and 29-33 are
            phosphorothioate thymidine (xi) SEQUENCE DESCRIPTION: SEQ ID NO: 150:

TTTTACCCTG ATGGTAGACG TTGGGGTGTT TTT                33

(2) INFORMATION FOR SEQ ID NO: 151:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (D) OTHER INFORMATION: All A's, C's, G's, U's are 2'OMe-
            nucleotide derivatives (ix) FEATURE:
        (A) NAME/KEY: modified base
        (B) LOCATION: 1..4, 29..33
        (D) OTHER INFORMATION: T's at positions 1-4 and 29-33
            are 2' deoxy phosphorothioate thymidine (xi) SEQUENCE DESCRIPTION: SEQ ID NO: 151:

TTTTACCCUG AUGGUAGACG CCGGGGUGTT TTT                33

(2) INFORMATION FOR SEQ ID NO: 152:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: modified base
        (B) LOCATION: 6..8, 19, 21..22
        (D) OTHER INFORMATION: C at positions 6-8, 19 and 21-22
            are 2'NH2 cytosine (ix) FEATURE:
        (A) NAME/KEY: modified base
        (B) LOCATION: 9, 12, 15, 27
        (D) OTHER INFORMATION: U at positions 9, 12, 15 and 27
            are 2'NH2 uracil (ix) FEATURE:
        (A) NAME/KEY: modified base
        (B) LOCATION: 5, 16
        (D) OTHER INFORMATION: A at positions 5 and 16 are 2'OMe
            adenine (ix) FEATURE:
        (A) NAME/KEY: modified base (B) LOCATION: 13, 17, 20, 23..26, 28
        (D) OTHER INFORMATION: G at positions 13, 17, 20, 23-26
            and 28 are 2'OMe guanosine (ix) FEATURE:
        (A) NAME/KEY: modified base
        (B) LOCATION: 1..4, 29..33
        (D) OTHER INFORMATION: T's at positions 1-4 and 29-33
            are 2' deoxy phosphorothioate thymidine (xi) SEQUENCE DESCRIPTION: SEQ ID NO: 152:

TTTTACCCUG AUGGUAGACG CCGGGGUGTT TTT                                33

(2) INFORMATION FOR SEQ ID NO: 153:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: modified base
        (B) LOCATION: 6..8, 19, 21..22
        (D) OTHER INFORMATION:  C at positions 6-8, 19 and 21-22
            are 2'NH2 cytosine (ix) FEATURE:
        (A) NAME/KEY: modified base
        (B) LOCATION: 5, 8, 11, 23
        (D) OTHER INFORMATION: U at positions 9, 12, 15 and 27
            are 2'NH2 uracil (ix) FEATURE:
        (A) NAME/KEY: modified base
        (B) LOCATION: 5, 16
        (D) OTHER INFORMATION: A at positions 5 and 16 are 2'OMe
            adenine (ix) FEATURE:
        (A) NAME/KEY: modified base
        (B) LOCATION: 13, 17, 20, 24..26, 28
        (D) OTHER INFORMATION: G at positions 13, 17, 20, 24-26
            and 28 are 2'OMe guanosine (ix) FEATURE:
        (A) NAME/KEY: modified base
        (B) LOCATION: 1..4, 29..33
        (D) OTHER INFORMATION: T's at positions 1-4 and 29-33
            are 2' deoxy phosphorothioate thymidine (xi) SEQUENCE DESCRIPTION: SEQ ID NO: 153:

TTTTACCCUG AUGGUAGACG CCGGGGUGTT TTT                                33

(2) INFORMATION FOR SEQ ID NO: 154:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: modified base
        (B) LOCATION: 6..8, 19, 21..22
        (D) OTHER INFORMATION:  C at positions 6-8, 19 and 21-22
            are 2'NH2 cytosine (ix) FEATURE:
        (A) NAME/KEY: modified base
        (B) LOCATION: 9, 12, 15, 27
        (D) OTHER INFORMATION: U at positions 9, 12, 15 and 27
            are 2'NH2 uracil (ix) FEATURE:

(A) NAME/KEY: modified base
          (B) LOCATION: 5, 16
          (D) OTHER INFORMATION: A at positions 5 and 16 are 2'OMe
              adenine (ix) FEATURE:
          (A) NAME/KEY: modified base
          (B) LOCATION: 13, 17, 20, 23..26, 28
          (D) OTHER INFORMATION: G at positions 13, 17, 20, 23-26
              and 28 are 2'OMe guanosine (ix) FEATURE:
          (A) NAME/KEY: modified base
          (B) LOCATION: 11
          (D) OTHER INFORMATION: A at position 11 is
              phosphorothioate adenine (ix) FEATURE:
          (A) NAME/KEY: modified base
          (B) LOCATION: 1..4, 29..33
          (D) OTHER INFORMATION: T's at positions 1-4 and 29-33
              are 2' deoxy phosphorothioate thymidine (xi) SEQUENCE DESCRIPTION: SEQ ID NO: 154:

TTTTACCCUG AUGGUAGACG CCGGGGUGTT TTT                                    33

(2) INFORMATION FOR SEQ ID NO: 155:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ix) FEATURE:
          (A) NAME/KEY: modified base
          (B) LOCATION: 2..4, 15, 17..18
          (D) OTHER INFORMATION:  C at positions 2-4, 15 and 17-18
              are 2'NH2 cytosine (ix) FEATURE:
          (A) NAME/KEY: modified base
          (B) LOCATION: 5, 8, 11, 23
          (D) OTHER INFORMATION: U at positions 5, 8, 11 and 23
              are 2'NH2 uracil (ix) FEATURE:
          (A) NAME/KEY: modified base
          (B) LOCATION: 9
          (D) OTHER INFORMATION: G at position 9 is a 2:1 misture
              of 2'OMe guanosine and 2'OH guanosine (ix) FEATURE:
          (A) NAME/KEY: modified base
          (B) LOCATION: 12, 14
          (D) OTHER INFORMATION: A at positions 12 and 14 are a
              2:1 mixture of 2'OMe adenine and 2'OH adenine (xi) SEQUENCE DESCRIPTION: SEQ ID NO: 155:

ACCCUGAUGG UAGACGCCGG GGUG                                              24

(2) INFORMATION FOR SEQ ID NO: 156:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ix) FEATURE:
          (A) NAME/KEY: modified base
          (B) LOCATION: 2..4, 15, 17..18
          (D) OTHER INFORMATION:  C at positions 2-4, 15 and 17-18
              are 2'NH2 cytosine

```
    (ix) FEATURE:
         (A) NAME/KEY: modified base
         (B) LOCATION: 5, 8, 11, 23
         (D) OTHER INFORMATION: U at positions 5, 8, 11 and 23
             are 2'NH2 uracil (ix) FEATURE:
         (A) NAME/KEY: modified base
         (B) LOCATION: 1, 7
         (D) OTHER INFORMATION: A at positions 1 and 7 are a 2:1
             mixture of 2'OMe adenine and 2'OH adenine (ix) FEATURE:
         (A) NAME/KEY: modified base
         (B) LOCATION: 19, 21
         (D) OTHER INFORMATION: G at positions 19 and 21 are a
             2:1 mixture of 2'OMe guanosine and 2'OH guanosine (xi) SEQUENCE DESCRIPTION: SEQ ID NO: 156:

ACCCUGAUGG UAGACGCCGG GGUG                                              24

(2) INFORMATION FOR SEQ ID NO: 157:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ix) FEATURE:
         (A) NAME/KEY: modified base
         (B) LOCATION: 2..4, 15, 17..18
         (D) OTHER INFORMATION:  C at positions 2-4, 15 and 17-18
             are 2'NH2 cytosine (ix) FEATURE:
         (A) NAME/KEY: modified base
         (B) LOCATION: 5, 8, 11, 23
         (D) OTHER INFORMATION: U at positions 5, 8, 11 and 23
             are 2'NH2 uracil (ix) FEATURE:
         (A) NAME/KEY: modified base
         (B) LOCATION: 6, 20, 24
         (D) OTHER INFORMATION: G at positions 6, 20, and 24 are
             a 2:1 mixture of 2'OMe guanosine and 2'OH guanosine (xi) SEQUENCE DESCRIPTION: SEQ ID NO: 157:

ACCCUGAUGG UAGACGCCGG GGUG                                              24

(2) INFORMATION FOR SEQ ID NO: 158:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ix) FEATURE:
         (A) NAME/KEY: modified base
         (B) LOCATION: 2..4, 15, 17..18
         (D) OTHER INFORMATION:  C at positions 2-4, 15 and 17-18
             are 2'NH2 cytosine (ix) FEATURE:
         (A) NAME/KEY: modified base
         (B) LOCATION: 5, 8, 11, 23
         (D) OTHER INFORMATION: U at positions 5, 8, 11 and 23
             are 2'NH2 uracil (ix) FEATURE:
         (A) NAME/KEY: modified base
         (B) LOCATION: 10, 13, 16
         (D) OTHER INFORMATION: G at positions 10, 13 and 16 are
             a 2:1 mixture of 2'OMe guanosine and 2'OH guanosine
```

(xi) SEQUENCE DESCRIPTION: SEQ ID NO: 158:

ACCCUGAUGG UAGACGCCGG GGUG    24

(2) INFORMATION FOR SEQ ID NO: 159:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 159:

ATCCGCCTGA TTAGCGATAC TACAACGGCG TGGAAGACTA GAGTGCAGCC    50

GAACGCATCT AACTTGAGCA AAATCACCTG CAGGGG    86

(2) INFORMATION FOR SEQ ID NO: 160:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 160:

ATCCGCCTGA TTAGCGATAC TACGCTACAA GTCCGCTGTG GTAGACAAGA    50

GTGCAGGCAA GACTTGAGCA AAATCACCTG CAGGGG    86

(2) INFORMATION FOR SEQ ID NO: 161:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 161:

ATCCGCCTGA TTAGCGATAC TAGGCCCGTC GAAGNTAGAG CGCAGGGCCC    50

CAAAATACCG ACTTGAGCAA ATCACCTGC AGGGG    85

(2) INFORMATION FOR SEQ ID NO: 162:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 162:

ATCCGCCTGA TTAGCGATAC TGTACCATCC ACGGTTTACG TGGACAAGAG    50

GGCCCTGGTA CACTTGAGCA AAATCACCTG CAGGGG    86

(2) INFORMATION FOR SEQ ID NO: 163:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 163:

ATCCGCCTGA TTAGCGATAC TTCACTACAA GTCCGCCGTG GTAGACAAGA    50

GTGCAGGCAA GACTTGAGCA AAATCACCTG CAGGGG    86

(2) INFORMATION FOR SEQ ID NO: 164:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 164:

```
ATCCGCCTGA TTAGCGATAC TACCGCTGTG TAGTTCCTTT AGGACTAGAG            50

GGCCGCCTAC ACTTGAGCAA AATCACCTGC AGGGG                            85
```

(2) INFORMATION FOR SEQ ID NO: 165:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 165:

```
ATCCGCCTGA TTAGCGATAC TTAGGCTTGA CGTCTTCTAG ACTAGAGTGC            50

AGTCAAACCC ACTTGAGCAA AATCACCTGC AGGGG                            85
```

(2) INFORMATION FOR SEQ ID NO: 166:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 166:

```
ATCCGCCTGA TTAGCGATAC TTGCAGGTCG ACTCTAGAGG ATCCCCGGGT            50

ACCGAGCTCG AACTTGAGCA AAATCACCTG CAGGGG                           86
```

(2) INFORMATION FOR SEQ ID NO: 167:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 167:

```
ATCCGCCTGA TTAGCGATAC TACGGTTTAC GTGGACAAGA GGGCCCTGGT            50

ACACTTGAGC AAAATCACCT GCAGGGG                                     77
```

(2) INFORMATION FOR SEQ ID NO: 168:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 168:

```
ATCCGCCTGA TTAGCGATAC TGGTGGACTA GAGGNCAGCA AACGATCCTT            50

GGTTCGCGTC CACTTGAGCA AAATCACCTG CAGGGG                           86
```

(2) INFORMATION FOR SEQ ID NO: 169:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 169:

ATCCGCCTGA TTAGCGATAC TTCAAGCACT CCCGTCTTCC AGACAAGAGT         50

GCAGGGCCTC TACTTGAGCA AAATCACCTG CAGGGG                        86

(2) INFORMATION FOR SEQ ID NO: 170:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 170:

ATCCGCCTGA TTAGCGATAC TCGTGATGGA CAAGAGGGCC CTATCCACCG         50

GATATCCGTC ACTTGAGCAA ATCACCTGC AGGGG                          85

(2) INFORMATION FOR SEQ ID NO: 171:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 171:

ATCCGCCTGA TTAGCGATAC TCAAGCAGTG CCCGTCTTCC AGACAAGAGT         50

GCAGGCCTCT ACTTGAGCAA ATCACCTGC AGGGG                          85

(2) INFORMATION FOR SEQ ID NO: 172:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 172:

ATCCGCCTGA TTAGCGATAC TTGATCCACC GTTTATAGTC CGTGGTAGAC         50

AAGAGTGCAG GACTTGAGCA AAATCACCTG CAGGGG                        86

(2) INFORMATION FOR SEQ ID NO: 173:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 173:

ATCCGCCTGA TTAGCGATAC TAACACACAA GAGGACAGTT ACAGGTAACA         50

TCCGCTCAGG ACTTGAGCAA ATCACCTGC AGGGG                          85

(2) INFORMATION FOR SEQ ID NO: 174:

(i) SEQUENCE CHARACTERISTICS:
        (A) LENGTH: 83 base pairs
        (B) TYPE: nucleic acid
        (C) STRANDEDNESS: single (D) TOPOLOGY: linear (xi) SEQUENCE DESCRIPTION: SEQ ID NO: 174:

ATCCGCCTGA TTAGCGATAC TAGTGGCGTC TATAGACAAG AGTGCAGCCC         50

GAGTTTCAAC TTGAGCAAAA TCACCTGCAG GGG                           83

(2) INFORMATION FOR SEQ ID NO: 175:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO: 175:

ATCCGCCTGA TTAGCGATAC TCCACAAGAG GGCAGCAAGT GTACAACTAC         50

AGCGTCCGGA CTTGAGCAAA ATCACCTGCA GGGG                          84

(2) INFORMATION FOR SEQ ID NO: 176:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO: 176:

CTACCTACGA TCTGACTAGC GCAGGGCCAC GTCTATTTAG ACTAGAGTGC         50

AGTGGTTCGC TTACTCTCAT GTAGTTCCT                                79

(2) INFORMATION FOR SEQ ID NO: 177:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 177:

CTACCTACGA TCTGACTAGC ACGGTCCAAA GGTTTCCCAT CCGTGGACTA         50

GAGGGCACGT GCTTAGCTTA CTCTCATGTA GTTCCT                        86

(2) INFORMATION FOR SEQ ID NO: 178:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 178:

CTACCTACGA TCTGACTAGC CCGTCGCGTG ACTATAACCA CACGCAGACT         50

AGAGTGCAGG GCTTAGCTTA CTCTCATGTA GTTCCT                        86

(2) INFORMATION FOR SEQ ID NO: 179:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO: 179:

| | |
|---|---|
| CTACCTACGA TCTGACTAGC CCGAATGGGG CTGCGACTGC AGTGGACGTC | 50 |
| ACGTCGTTAG CTTACTCTCA TGTAGTTCCT | 80 |

(2) INFORMATION FOR SEQ ID NO: 180:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO: 180:

| | |
|---|---|
| CTACCTACGA TCTGACTAGC ACGCAAGAGA GTCNCCGAAT GCAGTCTCAG | 50 |
| CCGCTAACAG CTTACTCTCA TGTAGTTCCT | 80 |

(2) INFORMATION FOR SEQ ID NO: 181:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO: 181:

| | |
|---|---|
| ATCCGCCTGA TTAGCGATAC TCANNNCACT GCAAGCAATT GTGGCCCAAA | 50 |
| GGGCTGAGTA CTTGAGCAAA ATCACCTGCA GGGG | 84 |

(2) INFORMATION FOR SEQ ID NO: 182:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 182:

| | |
|---|---|
| ATCCGCCTGA TTAGCGATAC TGCTCGCTTA CAAAAGGGAG CCACTGTAGC | 50 |
| CCAGACTGGA CACTTGAGCA AAATCACCTG CAGGGG | 86 |

(2) INFORMATION FOR SEQ ID NO: 183:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 183:

| | |
|---|---|
| ATCCGCCTGA TTAGCGATAC TGGTTATGGT GTGGTTCCGA ATGGTGGGCA | 50 |
| AAGTAACGCT TACTTGAGCA AAATCACCTG CAGGGG | 86 |

(2) INFORMATION FOR SEQ ID NO: 184:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 184:

| | |
|---|---|
| ATCCGCCTGA TTAGCGATAC TGCTTGTNGC TCCGAAGGGG CGCGTATCCA | 50 |
| AGGACGGTTC ACTTGAGCAA AATCACCTGC AGGGG | 85 |

(2) INFORMATION FOR SEQ ID NO: 185:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (xi) SEQUENCE DESCRIPTION: SEQ ID NO: 185:

```
ATCCGCCTGA TTAGCGATAC TTATGGAGTG GTTCCGAATG GTGGGCAAAG           50

TAACGCTTAC TTGAGCAAAA TCACCTGCAG GGG                             83
```

(2) INFORMATION FOR SEQ ID NO: 186:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 186:

```
CTACCTACGA TCTGACTAGC TGCNNGCGGG CGGTTCTCCG GATGGGACCA           50

TAAGGCTTTA GCTTAGCTTA CTCTCATGTA GTTCCT                          86
```

(2) INFORMATION FOR SEQ ID NO: 187:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO: 187:

```
CTACCTACGA TCTGACTAGC ACAAGGGGTC CTGNNGAATG GGGGAATACG           50

CTAGCCGAAG CTTACTCTCA TGTAGTTCCT                                 80
```

(2) INFORMATION FOR SEQ ID NO: 188:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 188:

```
CTACCTACGA TCTGACTAGC AACACGAGCA TGTGGGGTCC CTTCCGAATG           50

GGGGGTACAG GCTTAGCTTA CTCTCATGTA GTTCCT                          86
```

(2) INFORMATION FOR SEQ ID NO: 189:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 189:

```
CTACCTACGA TCTGACTAGC GAGGCATTAG GTCCGAATGG TAGTAATGCT           50

GTCGTGCCTT GCTTAGCTTA CTCTCATGTA GTTCCT                          86
```

(2) INFORMATION FOR SEQ ID NO: 190:

(i) SEQUENCE CHARACTERISTICS:

(A) LENGTH: 80 base pairs
        (B) TYPE: nucleic acid
        (C) STRANDEDNESS: single
        (D) TOPOLOGY: Linear (xi) SEQUENCE DESCRIPTION: SEQ ID NO: 190:

CTACCTACGA TCTGACTAGC CCGAATGGGG CTGCGACTGC AGTGGACGTC         50

ACGTCGTTAG CTTACTCTCA TGTAGTTCCT                              80

(2) INFORMATION FOR SEQ ID NO: 191:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 191:

CTACCTACGA TCTGACTAGC GAGGAGGTGC GTTGTCCGAA GGGGTCGTTA         50

GTCACCTCGT GCTTAGCTTA CTCTCATGTA GTTCCT                       86

(2) INFORMATION FOR SEQ ID NO: 192:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO: 192:

CTACCTACGA TCTGACTAGC GCAAGGGGTC CTGCCGAATG GGGGAATACG         50

CTAGCCGAAA GCTTACTCTC ATGTAGTTCC T                            81

(2) INFORMATION FOR SEQ ID NO: 193:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO: 193:

CTACCTACGA TCTGACTAGC ATCCTTCCGA ATGGGGGAAA TGGCGNCCCA         50

GCTTACTCTC ATGTAGTTCC T                                       71

(2) INFORMATION FOR SEQ ID NO: 194:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (xi) SEQUENCE DESCRIPTION: SEQ ID NO: 194:

CTACCTACGA TCTGACTAGC ACGCAAGAGA GGTCNCCGAA TGGCAGTCTC         50

AGCCGCTAAC AGCTTACTCT CATGTAGTTC CT                           82

(2) INFORMATION FOR SEQ ID NO: 195:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 195:

CTACCTACGA TCTGACTAGC CACGATAATC CTCCGAAAGC GTTGTCCGAA     50

TGGGTCGTTA GCTTAGCTTA CTCTCATGTA GTTCCT                   86

(2) INFORMATION FOR SEQ ID NO: 196:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 196:

ATCCGCCTGA TTAGCGATAC TTATCACCCC CACTGGATAG AGCCGCAGCG     50

TGCCCCTACT ACTTGAGCAA AATCACCTGC AGGGG                    85

(2) INFORMATION FOR SEQ ID NO: 197:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 197:

ATCCGCCTGA TTAGCGATAC TGCCCACTGC ATAGAGGGAC GGTTGTTTCC     50

GCCCGGTGTT TACTTGAGCA AAATCACCTG CAGGGG                   86

(2) INFORMATION FOR SEQ ID NO: 198:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO: 198:

CTACCTACGA TCTGACTAGC GTGAAGGAGC CCCAACTGGA TAGAAGCCTT     50

AAGGCGGTGT GCTTACTCTC ATGTAGTTCC T                        81

(2) INFORMATION FOR SEQ ID NO: 199:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 199:

CTACCTACGA TCTGACTAGC CCACCGCAGA GTGTTACACC CCATAGGAGA     50

AGTCCGGATG GCTTAGCTTA CTCTCATGTA GTTCCT                   86

(2) INFORMATION FOR SEQ ID NO: 200:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO: 200:

CTACCTACGA TCTGACTAGC CCACTGCATA GAGAGTCGCA AGACACGGTG     50

```
CTTTATTCNC CGCTTAGCTT ACTCTCATGT AGTTCCT                                  87

(2) INFORMATION FOR SEQ ID NO: 201:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 201:

CTACCTACGA TCTGACTAGC TGCCCCACTG GATAGAGTAG GAGGCCTAGC                    50

CGACACGGTG CTTAGCTTAC TCTCATGTAG TTCCT                                    85

(2) INFORMATION FOR SEQ ID NO: 202:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 202:

CTACCTACGA TCTGACTAGC CGAGGTCCCC CACTGGATAG AGTTGTTGAA                    50

ACAACGGTGC GCTTAGCTTA CTCTCATGTA GTTCCT                                   86

(2) INFORMATION FOR SEQ ID NO: 203:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 203:

CTACCTACGA TCTGACTAGC AACACTTCCC CACTGGATAG AGGCCTTTCG                    50

CAGAGCCGGT GCTTAGCTTA CTCTCATGTA GTTCCT                                   86

(2) INFORMATION FOR SEQ ID NO: 204:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 204:

CTACCTACGA TCTGACTAGC CCACTGCATA GAGAACTGGA TCGACGGTCC                    50

AAAGTTCGGT GCTTAGCTTA CTCTCATGTA GTTCCT                                   86

(2) INFORMATION FOR SEQ ID NO: 205:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (xi) SEQUENCE DESCRIPTION: SEQ ID NO: 205:

CTACCTACGA TCTGACTAGC CCACTGCATA GAGATACTGG ATTCGACNNN                    50

CCAAAGTTTC GGTGCTTAGC TTACTCTCAT GTAGTTCCT                                89
```

(2) INFORMATION FOR SEQ ID NO: 206:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 206:

```
CTACCTACGA TCTGACTAGC CCACTGCAGA GAGTCAACCT TACGANGCCA        50

AGGTTGCGGT GCTTAGCTTA CTCTCATGTA GTTCCT                       86
```

(2) INFORMATION FOR SEQ ID NO: 207:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 207:

```
ATCCGCCTGA TTAGCGATAC TTCTGCGAGA GACCTACTGG AACGTTTTGT        50

GATATTCACA ACTTGAGCAA AATCACCTGC AGGGG                        85
```

(2) INFORMATION FOR SEQ ID NO: 208:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 208:

```
ATCCGCCTGA TTAGCGATAC TATACACCCG GCGGGCCTAC CGGATCGTTG        50

ATTTCTCTCC ACTTGAGCAA AATCACCTGC AGGGG                        85
```

(2) INFORMATION FOR SEQ ID NO: 209:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 209:

```
ATCCGCCTGA TTAGCGATAC TACGCCCCCT GAGACCTACC GGAATNTTNT        50

CGCTAGGCCT AACTTGAGCA AAATCACCTG CAGGGG                       86
```

(2) INFORMATION FOR SEQ ID NO: 210:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 210:

```
ATCCGCCTGA TTAGCGATAC TGGGCATCTA ACCCAGACCT ACCGGAACGT        50

TATCGCTTGT GACTTGAGCA AAATCACCTG CAGGGG                       86
```

(2) INFORMATION FOR SEQ ID NO: 211:

(i) SEQUENCE CHARACTERISTICS:
        (A) LENGTH: 83 base pairs (B) TYPE: nucleic acid
          (C) STRANDEDNESS: single
          (D) TOPOLOGY: linear (xi) SEQUENCE DESCRIPTION: SEQ ID NO: 211:

ATCCGCCTGA TTAGCGATAC TGGTGTGAAC CAGACCTACN GGAACGTTAT          50

CGCTTGTGAC TTGAGCAAAA TCACCTGCAG GGG                            83

(2) INFORMATION FOR SEQ ID NO: 212:

(i) SEQUENCE CHARACTERISTICS:
          (A) LENGTH: 86 base pairs
          (B) TYPE: nucleic acid
          (C) STRANDEDNESS: single
          (D) TOPOLOGY: linear (xi) SEQUENCE DESCRIPTION: SEQ ID NO: 212:

ATCCGCCTGA TTAGCGATAC TCATCAGTAT TATATAACGG GAACCAACGG          50

CAAATGCTGA CACTTGAGCA AAATCACCTG CAGGGG                         86

(2) INFORMATION FOR SEQ ID NO: 213:

(i) SEQUENCE CHARACTERISTICS:
          (A) LENGTH: 85 base pairs
          (B) TYPE: nucleic acid
          (C) STRANDEDNESS: single
          (D) TOPOLOGY: linear (xi) SEQUENCE DESCRIPTION: SEQ ID NO: 213:

ATCCGCCTGA TTAGCGATAC TTCCNNGGGA GAATAGGGTT AGTCGGAGAA          50

GTTAATCGCT ACTTGAGCAA AATCACCTGC AGGGG                          85

(2) INFORMATION FOR SEQ ID NO: 214:

(i) SEQUENCE CHARACTERISTICS:
          (A) LENGTH: 86 base pairs
          (B) TYPE: nucleic acid
          (C) STRANDEDNESS: single
          (D) TOPOLOGY: linear (xi) SEQUENCE DESCRIPTION: SEQ ID NO: 214:

ATCCGCCTGA TTAGCGATAC TCGGGAACGT GTGGTTACNC GGCCTACTGG          50

ATTGTTTCCT GACTTGAGCA AAATCACCTG CAGGGG                         86

(2) INFORMATION FOR SEQ ID NO: 215:

(i) SEQUENCE CHARACTERISTICS:
          (A) LENGTH: 81 base pairs
          (B) TYPE: nucleic acid
          (C) STRANDEDNESS: single
          (D) TOPOLOGY: linear (xi) SEQUENCE DESCRIPTION: SEQ ID NO: 215:

ATCCGCCTGA TTAGCGATAC TGGTAGGTCC GGTGTGAAAG AGGTTCGCAT          50

CAGGTAACTT GAGCAAAATC ACCTGCAGGG G                              81

(2) INFORMATION FOR SEQ ID NO: 216:

(i) SEQUENCE CHARACTERISTICS:
          (A) LENGTH: 85 base pairs
          (B) TYPE: nucleic acid
          (C) STRANDEDNESS: single
          (D) TOPOLOGY: linear (xi) SEQUENCE DESCRIPTION: SEQ ID NO: 216:

ATCCGCCTGA TTAGCGATAC TCCTCAGGCA ACATAGTTGA GCATCGTATC    50

GATCCTGGAG ACTTGAGCAA AATCACCTGC AGGGG    85

(2) INFORMATION FOR SEQ ID NO: 217:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO: 217:

ATCCGCCTGA TTAGCGATAC TTTGGCTTGA GTCCCGGGAC GCACTGTTGA    50

CAGTGGAGTA CTTGAGCAAA ATCACCTGCA GGGG    84

(2) INFORMATION FOR SEQ ID NO: 218:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 218:

ATCCGCCTGA TTAGCGATAC TCAGCAGGTT AGTATAACGG GAACCAACGG    50

CAAATGCTGA CACTTGAGCA AAATCACCTG CAGGGG    86

(2) INFORMATION FOR SEQ ID NO: 219:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 219:

CTACCTACGA TCTGACTAGC GCAAGGGCAT CTCGGAATCG GTTAATCTGA    50

CTTGCAATAC GCTTAGCTTA CTCTCATGTA GTTCCT    86

(2) INFORMATION FOR SEQ ID NO: 220:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO: 220:

CTACCTACGA TCTGACTAGC GATCCACGAA GAAGCTTACT CTCATGTAGT    50

TCCAGCTTAC TCTCATGTAG TTCCT    75

(2) INFORMATION FOR SEQ ID NO: 221:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 221:

GTACCATCCA CGGTTTACGT GGACAAGAGG GCCCTGGTAC    40

(2) INFORMATION FOR SEQ ID NO: 222:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 222:

GTAGTTCCTT TAGGACTAGA GGGCCGCCTA C                           31

(2) INFORMATION FOR SEQ ID NO: 223:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 223:

TGGACTAGAG GNCAGCAAAC GATCCTTGGT TCGCGTCC                    38

(2) INFORMATION FOR SEQ ID NO: 224:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 224:

CCCGTCTTCC AGACAAGAGT GCAGGG                                 26

(2) INFORMATION FOR SEQ ID NO: 225:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 225:

AGGGCCACGT CTATTTAGAC TAGAGTGCAG TGGTTC                      36

(2) INFORMATION FOR SEQ ID NO: 226:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 226:

GGAGGTGCGT TGTCCGAAGG GGTCGTTAGT CACCTC                      36

(2) INFORMATION FOR SEQ ID NO: 227:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 227:

GCAAGGGGTC CTGCCGAATG GGGGAATACG CTAGCCGAAA                  40

(2) INFORMATION FOR SEQ ID NO: 228:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 228:

CGAGGTCCCC CACTGGATAG AGTTGTTGAA ACAACGGTGC GCTTA             45

(2) INFORMATION FOR SEQ ID NO: 229:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 229:

AACACTTCCC CACTGGATAG AGGCCTTTCG CAGAGCCGGT GCTTA             45

(2) INFORMATION FOR SEQ ID NO: 230:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 230:

GGGCATCTAA CCCAGACCTA CCGGAACGTT ATCGCTTGTG                  40

(2) INFORMATION FOR SEQ ID NO: 231:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 231:

AGACAAGAGT GCAGG                                                 15

(2) INFORMATION FOR SEQ ID NO: 232:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 232:

GGACTAGAGG GCAGT                                                 15

(2) INFORMATION FOR SEQ ID NO: 233:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 233:

CTCCGAATGG GGGNAAAG                                           18

(2) INFORMATION FOR SEQ ID NO: 234:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 234:

CCCCACTGGA TAGAG                                                          15

(2) INFORMATION FOR SEQ ID NO: 235:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 235:

CCCCACTGCA TAGAG                                                          15

(2) INFORMATION FOR SEQ ID NO: 236:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 236:

AGACCTACCG GAACGTT                                                        17

(2) INFORMATION FOR SEQ ID NO: 237:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 237:

ATCCGCCTGA TTAGCGATAC TNNNNNNNNN NNNNNNNNNN NNNNNNNNNN                    50

NNNNNNNNNN NACTTGAGCA AAATCACCTG CAGGGG                                   86

(2) INFORMATION FOR SEQ ID NO: 238:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ix) FEATURE:
        (A) NAME/KEY:  modified base
        (B) LOCATION:  1..3
        (D) OTHER INFORMATION:  N at positions 1-3 is biotin (xi) SEQUENCE DESCRIPTION: SEQ ID NO: 238:

NNNCCCCTGC AGGTGATTTT GCTCAAGT                                            28

(2) INFORMATION FOR SEQ ID NO: 239:

(i) SEQUENCE CHARACTERISTICS:
        (A) LENGTH: 21 base pairs
        (B) TYPE: nucleic acid
        (C) STRANDEDNESS: single
        (D) TOPOLOGY: linear -continued (xi) SEQUENCE DESCRIPTION: SEQ ID NO: 239:

ATCCGCCTGA TTAGCGATAC T                                              21

(2) INFORMATION FOR SEQ ID NO: 240:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO: 240:

CTACCTACGA TCTGACTAGC NNNNNNNNNN NNNNNNNNNN NNNNNNNNNN                50

NNNNNNNNNN GCTTACTCTC ATGTAGTTCC T                                    81

(2) INFORMATION FOR SEQ ID NO: 241:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ix) FEATURE:
        (A) NAME/KEY:  modified base
        (B) LOCATION:  2, 4
        (D) OTHER INFORMATION:  N at positions 2 and 4 is biotin (xi) SEQUENCE DESCRIPTION: SEQ ID NO: 241:

ANANAGGAAC TACATGAGAG TAAGC                                           25

(2) INFORMATION FOR SEQ ID NO: 242:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 242:

CTACCTACGA TCTGACTAGC                                                 20

HIGH-AFFINITY OLIGONUCLEOTIDE LIGANDS TO VASCULAR ENDOTHELIAL GROWTH FACTOR (VEGF)

RELATED APPLICATIONS

This application is a Continuation of U.S. patent application Ser. No. 09/156,824, filed Sep. 18, 1998, now abandoned entitled "High Affinity Oligonucleotide Ligands to Vascular Endothelial Growth Factor", which is a continuation of Ser. No. 08/447169, filed May 19, 1995, now U.S. Pat. No. 5,811,533 entitled "High-Affinity Oligonucleotide Ligands to Vascular Endothelial Growth Factor (VEGF)," which is a Continuation-in-Part of U.S. patent application Ser. No. 07/714,131, filed Jun. 10, 1991, entitled "Nucleic Acid Ligands," now U.S. Pat. No. 5,475,096, which is a Continuation-in-Part of U.S. patent application Ser. No. 07/536,428, filed Jun. 11, 1990, entitled "Systematic Evolution of Ligands by Exponential Enrichment," now abandoned. This application is a Continuation-in-Part of U.S. patent application Ser. No. 08/205,515, filed Mar. 3, 1994, now abandoned in favor of U.S. patent application Ser. No. 08/233,012, filed Apr. 25, 1994, entitled "High-Affinity Oligonucleotide Ligands to Vascular Endothelial Growth Factor (VEGF)," and a Continuation-in-Part of U.S. patent application Ser. No. 07/964,624, filed Oct. 21, 1992 entitled "Nucleic Acid Ligands to HIV-RT and HIV-1 Rev," now U.S. Pat. No. 5,496,938. All applications cited herein are expressly incorporated in their entirety by this reference.

FIELD OF THE INVENTION

Described herein are high affinity nucleic acid ligands to vascular endothelial growth factor (VEGF). The method utilized herein for identifying such nucleic acid ligands is called SELEX, an acronym for Systematic Evolution of Ligands by EXponential enrichment

BACKGROUND OF THE INVENTION

Neovascularization or angiogenesis is the process in which sprouting new blood vessels are formed from the existing endothelium in response to external stimuli that signal inadequate blood supply. Angiogenesis is generally rare under normal physiological conditions but frequently accompanies certain pathological conditions such as psoriasis, rheumatoid arthritis, hemangioma, and solid tumor growth and metastasis (Folkman & Klagsbrun (1987) Science 235:442–447; Kim et al. (1993) Nature 362:841–844). Several growth factors that are capable of inducing angiogenesis in vivo have been identified to date including acidic and basic fibroblast growth factors (aFGF, bFGF), transforming growth factors α and β (TGFα, TGFβ), platelet derived growth factor (PDGF), angiogenin, platelet-derived endothelial cell growth factor (PD-ECGF), interleukin-8 (IL-8), and vascular endothelial growth factor (VEGF).

VEGF was originally purified from guinea pig ascites and tumor cell cultures as a factor that increases vascular permeability (Senger, D. R. et al. (1983) Science 219:983–985) and it has therefore also been referred to as vascular permeability factor (VPF). VEGF is a heat and acid-stable, disulfide-linked homodimer. Four isoforms have been described (121, 165, 189 and 206 amino acids, respectively) and are believed to be the result of alternative splicing of mRNA. Despite the presence of an identical N-terminal hydrophobic signal sequence in all molecular isoforms of VEGF, only the two lower molecular weight species are efficiently secreted (Ferrara, N. et al. (1991) J. Cell. Biochem. 47:211–218). The predominant VEGF isoform in most cells and tissues is the 165 amino acid species. Although VEGF is typically glycosylated, glycosylation is only required for efficient secretion but not for activity (Yeo, T-.K. et al. (1991) Biochem. Biophys. Res. Commun. 179:1568–1575; Peretz, D. et al. (1992) Biochem. Biophys. Res. Commun. 182:1340–1347). The amino acid sequence of VEGF is highly conserved across species and exhibits a modest but significant homology (18–20%) to PDGF A and B (Jakeman L. B. et al. (1992) J. Clin. Invest. 89:244–253; Ferrara et al. (1992) Endocrine Rev. 13:18–32).

Unlike other angiogenic growth factors, target cell specificity of VEGF is limited to vascular endothelial cells. The biological actions of VEGF are mediated through its interaction with specific cell-associated receptors which have been identified in the majority of tissues and organs (Jakeman, L. B. (1992) J. Clin. Invest. 89:244–253). Three high-affinity receptors for VEGF have been cloned to date: flt1, kdr/flk-1 and flt4 (Vaisman, N. et al. (1990) J. Biol. Chem. 265:19461–19466; de Vries, C. et al. (1992) Science 255:989–991; Galland, F. et al. (1993) Oncogene 8:1233–1240). These receptors belong to a family of transmembrane tyrosine kinases and bind VEGF with dissociation constants between $10^{-11}$ M to $10^{-12}$ M. Recent experiments have shown that binding of VEGF to its high-affinity receptors is significantly enhanced by heparin or cell surface-associated heparin-like molecules (Gitay-Goren, H. (1992) J. Biol. Chem. 267:6093–6098).

In addition to promoting the growth of vascular endothelial cells and inducing vascular leakage, VEGF is also known to induce the proteolytic enzymes interstitial collagenase, urokinase-type plasminogen activator (uPA) and tissue-type plasminogen activator (tPA) (Unemori E. et al. (1993) J. Cell. Physiology 153:557; Pepper, M. S. et al. (1992) Biochem. Biophys. Res. Commun. 189:824). These enzymes are known to play a prominent role in angiogenesis-related extracellular matrix degradation.

As a secreted and specific mitogen for endothelial cells, VEGF may be one of the major angiogenesis inducers in vivo. Several recent observations have supported this notion. For example, the expression of VEGF and its receptors accompanies angiogenesis associated with (i) embryonic development (Breier, G. et al. (1992) Development 114:521–532), (ii) hormonally-regulated reproductive cycle and (iii) tumor growth (Dvorak, H. F. (1991) J. Exp. Med. 174:1275–1278; Shweiki, D. et al. (1992) Nature 359:843–845; Plate, K. H. et al. (1992) Nature 359:845–848). It is relevant to note that aggressive tumor growth is accompanied by the generation of necrotic areas where oxygen and nutrient supplies are inadequate. Oxygen deprivation hypoxia) in tissues is a known angiogenesis stimulant. Interestingly, VEGF expression was found to be the highest in tumor cells facing the necrotic areas (Shweiki, D. et al. (1992) supra; Plate, K. H. et al. (1992) supra). It has therefore been suggested by these authors that VEGF plays a key role in hypoxia-induced angiogenesis.

Recent experiments with neutralizing monoclonal antibodies (MAbs) to VEGF have been especially meaningful for establishing that this growth factor is an important tumor angiogenesis inducer in vivo (Kim, K. J. et al. (1993) Nature 362:841–844). Immunocompromised (nude) mice injected with human rhabdomyosarcoma, glioblastoma or leiomyosarcoma cell lines rapidly develop tumors. Specific neutralizing MAb to VEGF were found to inhibit the growth of these tumors. The density of tumor vasculature was decreased in MAb-treated animals as compared to controls. The same MAb, on the other hand, had no effect on the growth rate of the tumor cells in vitro suggesting that the growth inhibition was not mediated at the cellular level and appears to be mediated by the 165-amino acid isoform of VEGF.

BRIEF SUMMARY OF THE INVENTION

Herein described is the isolation and characterization of binding properties of a set of high-affinity nucleic acid ligands to VEGF. RNA, modified RNA, and ssDNA ligands are provided by the present invention. These ligands were selected from an initial pool of about $10^{14}$ RNA or DNA molecules randomized at thirty or forty contiguous positions. The evolved RNA ligands shown in FIGS. 2A–F bind VEGF with affinities in the low nanomolar range.

Also included herein are modified RNA ligands to VEGF. Such modified RNA ligands may be prepared after the identification of 2'-OH RNA ligands or by performing SELEX using a candidate mixture of modified RNAs. For example, 2'-$NH_2$ pyrimidine RNA ligands to VEGF are described herein and the evolved ligands are shown in FIG. 9. Additionally post-SELEX modified RNA ligands are provided in Table 4.

Also included herein are ssDNA ligands to VEGF. The evolved ssDNA ligands are shown in Table 8.

The present invention includes the method of identifying nucleic acid ligands and ligand sequences to VEGF comprising:

a) contacting a candidate mixture of nucleic acids with VEGF, wherein nucleic acids having an increased affinity to VEGF relative to the candidate mixture may be partitioned from the remainder of the candidate mixture;

b) partitioning the increased affinity nucleic acids from the remainder of the candidate mixture; and c) amplifying the increased affinity nucleic acids, whereby nucleic acid ligands to VEGF may be identified.

BRIEF DESCRIPTION OF THE FIGURES

FIG. 1 shows the starting RNA and PCR primers used in the SELEX experiment described in Examples 1 and 2.

FIGS. 2A–F show the aligned sequences and predicted secondary structures for the six families (grouped by primary sequence homology) of RNA ligands to VEGF. Arrows underline the inverted repeats of the double stranded (stem) regions. Lowercase and uppercase letters are used to distinguish nucleotides in the constant and the evolved sequence regions, respectively. Positions are numbered consecutively starting (arbitrarily) with the evolved nucleotide closest to the 5' end of the shown window.

FIG. 8 shows the starting random RNAs for experiments A and B, and PCR primers used in identifying 2'-NH,-RNA ligands to VEGF (Example 4).

FIGS. 9A–G show 2'-$NH_2$-RNA ligands to VEGF identified via the SELEX technology as described in Example 4.

DETAILED DESCRIPTION OF THE INVENTION

Figure 3C:
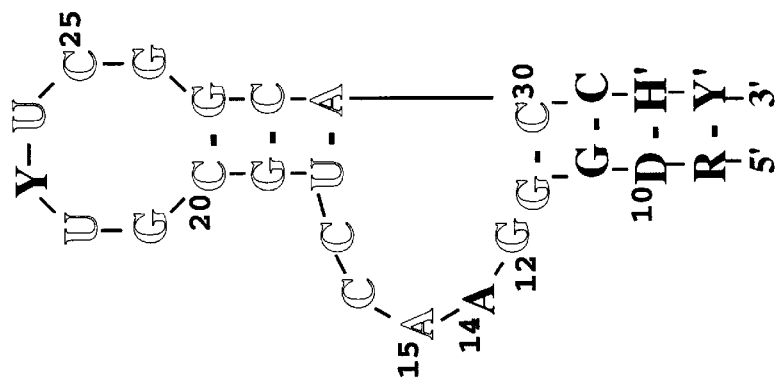
FIGS. 3A–F show the consensus sequences and predicted secondary structures for certain of the VEGF ligand families. Plain text is used to designate positions that occur at >60% but <80% frequencies. Positions where individual nucleotides are strongly conserved (frequencies>80%) are outlined. Residues in parenthesis occur at that position with equal frequencies to gaps. The numbering system described in the legend to FIG. 2 is used. R=A or G; Y=C or U; M=A or C; D=A, G or U; V=G, A or C; S=G or C; K=G or U; N=any base and prime (') indicates a complementary base.
Figure 3B:
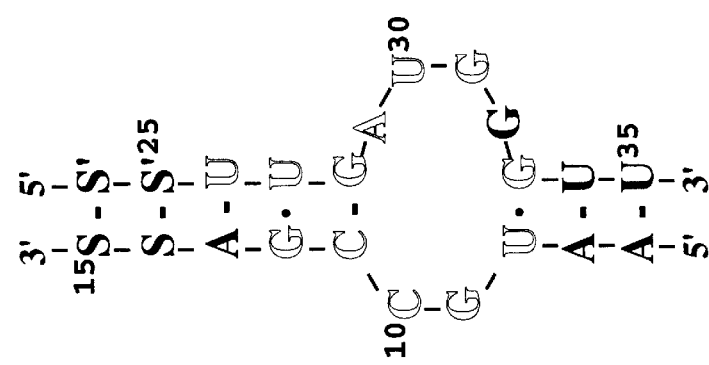
Figure 3A:
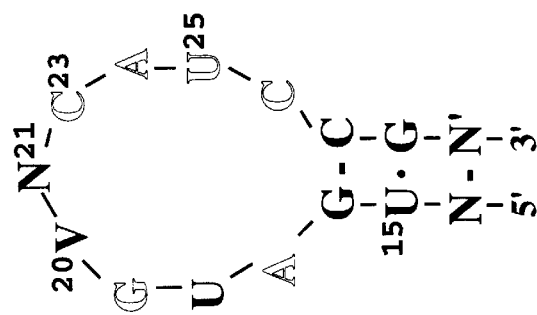
Figure 3F:
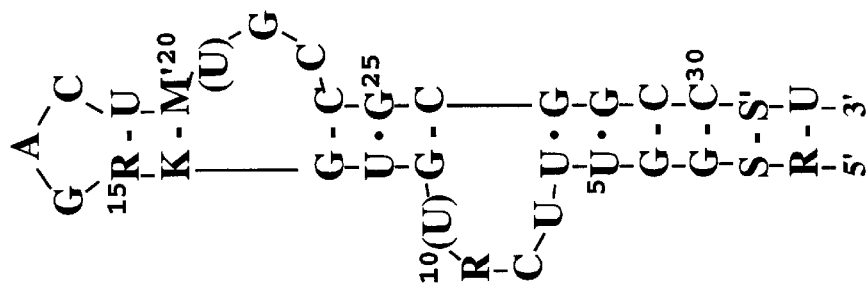
Figure 3E:
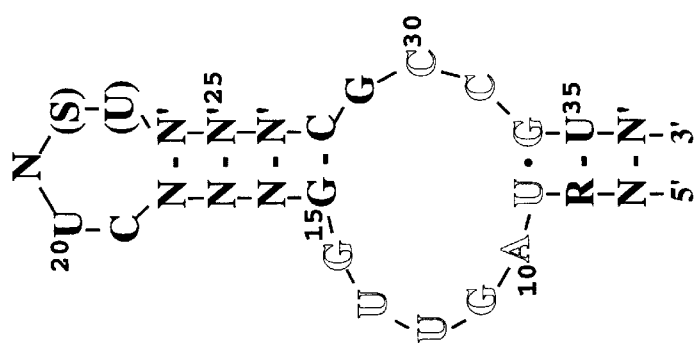
Figure 3D:
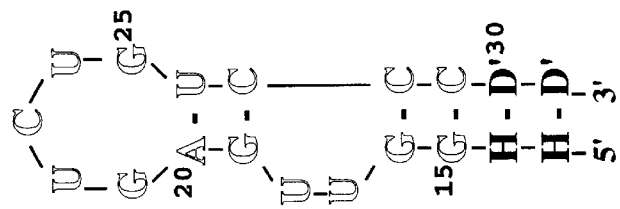
Figure 4A:
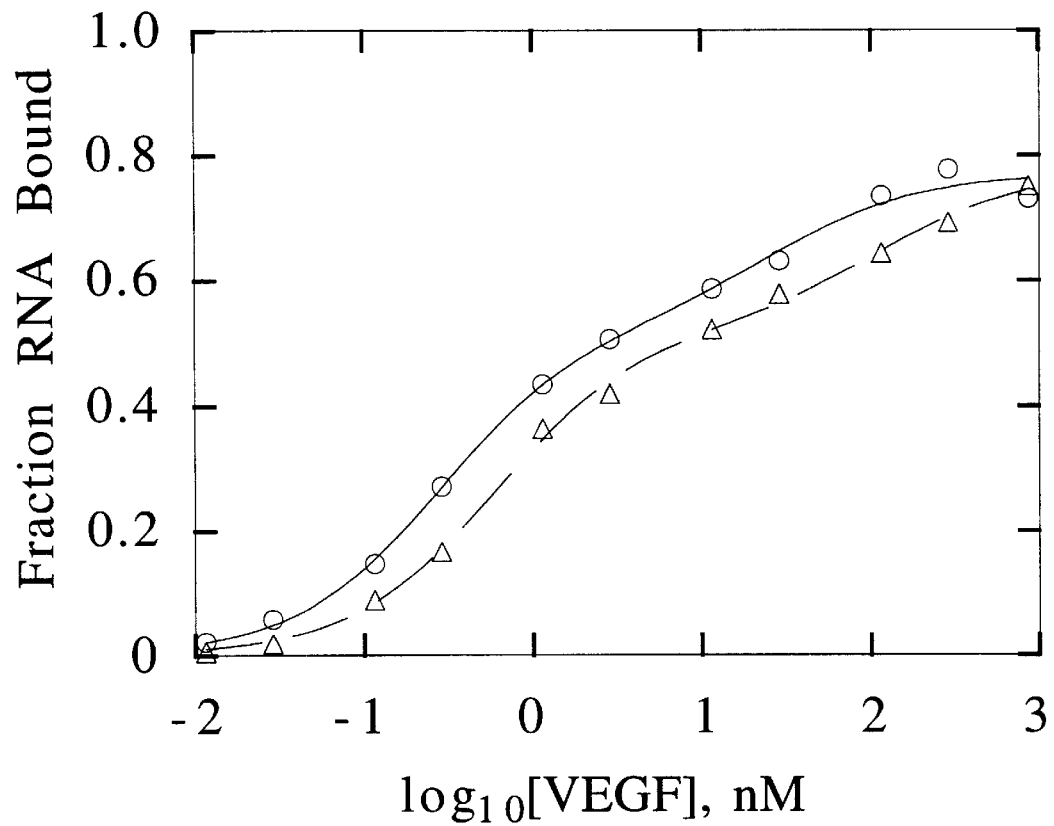
FIGS. 4A–F show the binding curves for a representative set of high-affinity ligands to VEGF. Full-length (○) and truncated (Δ) ligands tested were 100 (SEQ ID NO:11) and 100t (SEQ ID NO:51) (family 1, FIG. 4A), 44 (SEQ ID NO:20) and 44t (SEQ ID NO:52) (family 2, FIG. 4B), 12 (SEQ ID NO:22) and 12t (SEQ ID NO:53) (family 3, FIG. 4C), 40 (SEQ ID NO:28) and 40t (SEQ ID NO:54) (family 4, FIG. 4D), 84 (SEQ ID NO:36) and 84t (SEQ ID NO:55) (family 5, FIG. 4E), and 126 (SEQ ID NO:38) and 126t (SEQ ID NO:56) (family 6, FIG. 4F). The fraction of $^{32}$P-labeled RNA bound to nitrocellulose filters is plotted as a function of total protein concentration and the lines represent the fit of the data points to eq. 2 (40t, 84 and 84t) or to eq. 5 (all other ligands). RNA concentrations were determined from their absorbance reading at 260 nm (and were typically<50 pM). Binding reactions were done at 37° C. in phosphate buffered saline containing 0.01% human serum albumin FIGS. 5A and B show the results of the determination of the 3'- and 5'-boundaries for a representative high-affinity VEGF ligand (ligand 12) (SEQ ID NO:50). The 3'-boundary determination (FIG. 5A) showing partially hydrolyzed 5'-end labeled RNA (lane 4), hydrolytic fragments retained on nitrocellulose filters following incubation of the partially hydrolyzed RNA with VEGF at 5 nM (lane 1), 0.5 nM (lane 2), or 0.125 nM (lane 3) and partial digest of the 5'-end labeled RNA with RNAse $T_1$ (lane 5) resolved on an 8% denaturing polyacrylamide gel. The 5'-boundary (FIG. 5B) was determined in an identical manner except that RNA radiolabeled at the 3'-end was used. Shown are RNase $T_1$ digest (lane 1), partial alkaline hydrolysis (lane 2), and hydrolytic fragments retained on nitrocellulose filters following incubation with VEGF at 5 nM (lane 3), 0.5 nM (lane 4), or 0.125 nM (lane 5). Arrows indicate the 3'- and the 5'-boundaries of the minimal ligand 12 (italicized).
Figure 4B:
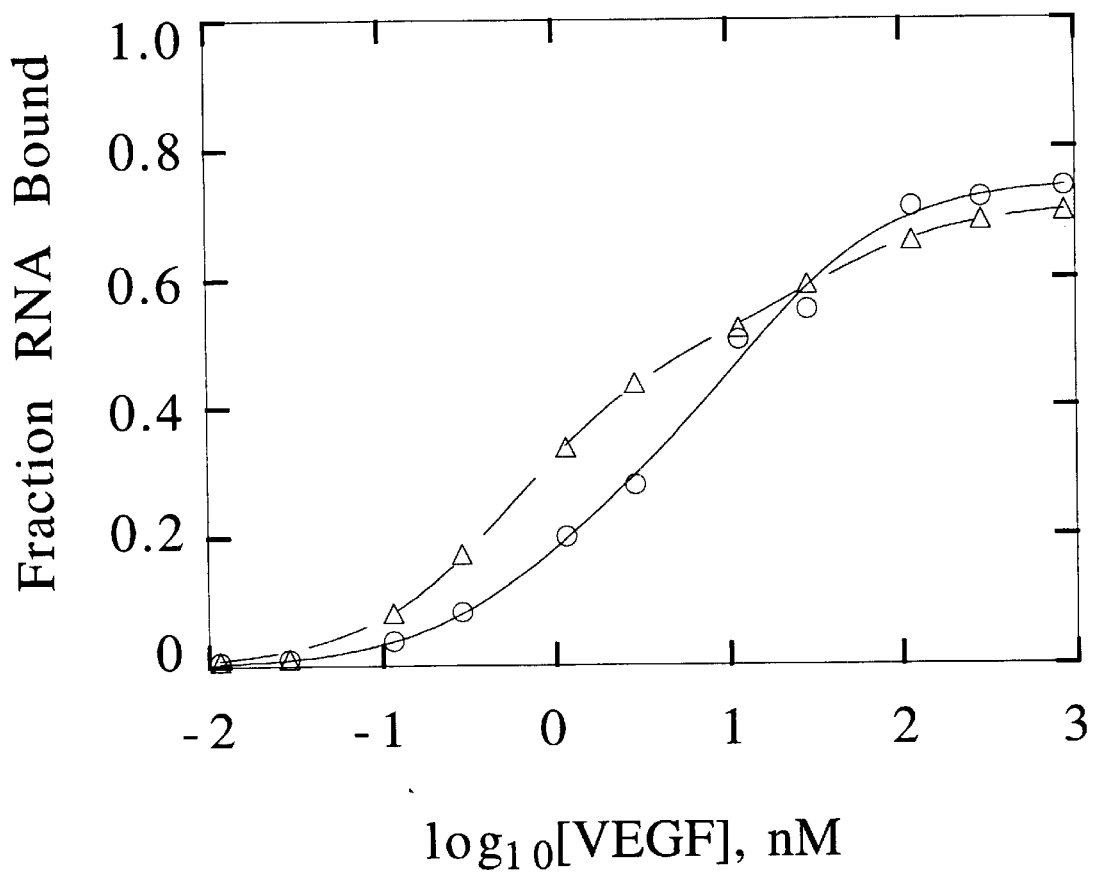
Figure 4C:
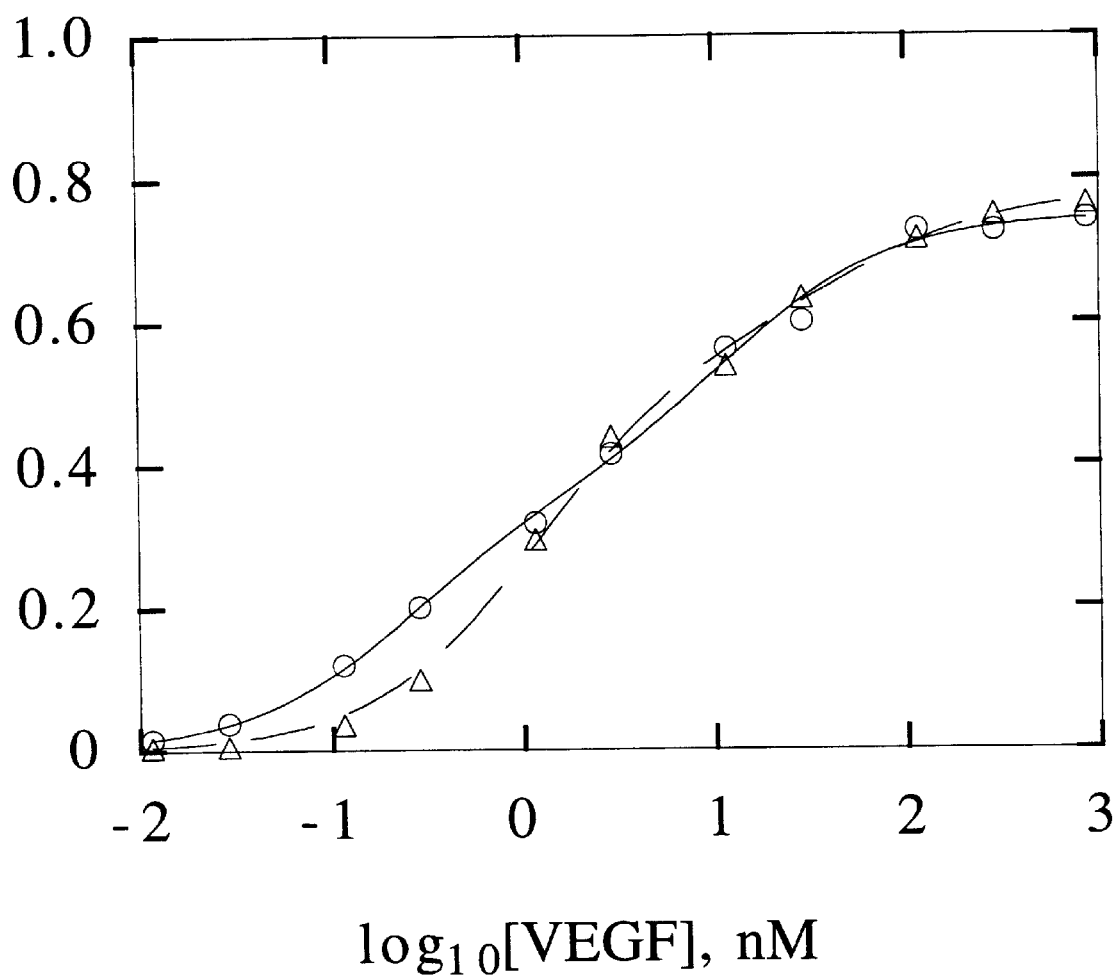
Figure 4D:
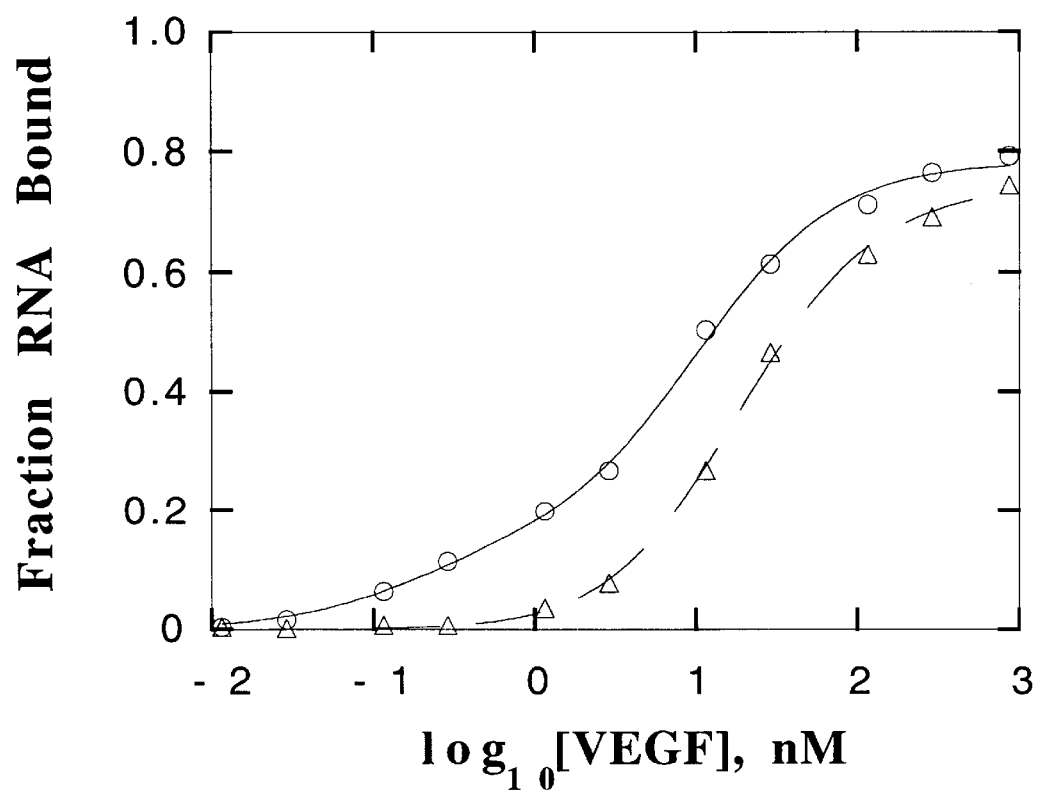
Figure 4E:
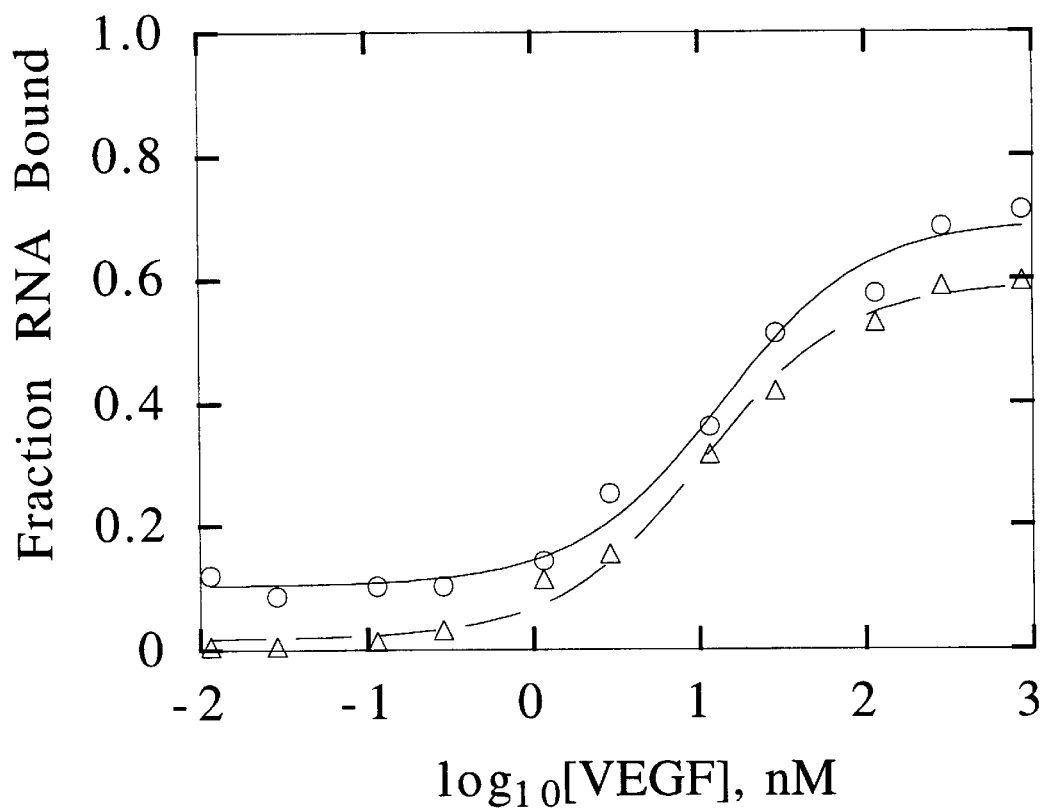
Figure 4F:
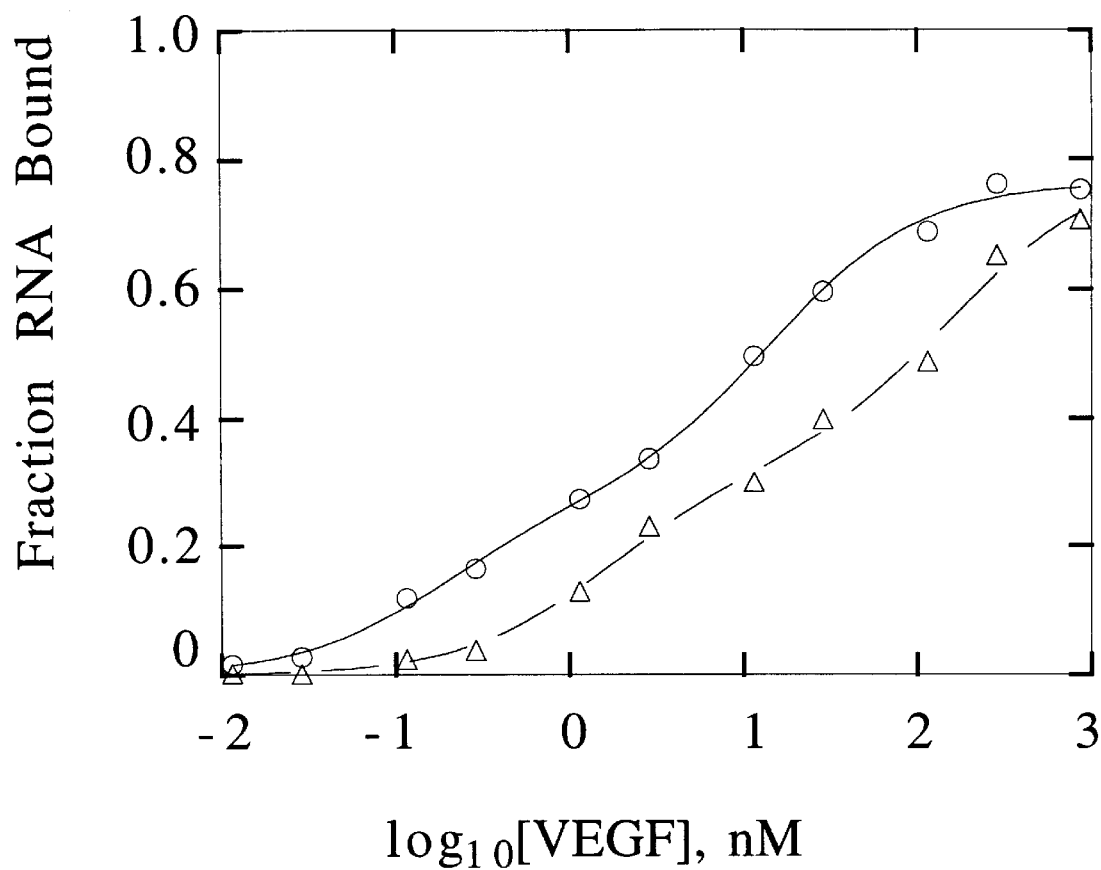

This application describes high-affinity nucleic acid ligands to vascular endothelial growth factor (VEGF) identified through the method known as SELEX The SELEX method is described in detail in U.S. patent application Ser. No. 07/536,428, filed Jun. 11, 1990, entitled "Systematic Evolution of Ligands by EXponential Enrichment," now abandoned, U.S. patent application Ser. No. 07/714,131, filed Jun. 10, 1991, entitled "Nucleic Acid Ligands," now U.S. Pat. No. 5,475,096, U.S. patent application Ser. No. 07/931,473, filed Aug. 17, 1992, entitled "Methods for Identifying Nucleic Acid Ligands," now U.S. Pat. No. 5,270,163.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below, b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target 5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets where the protein is and is not a nucleic acid binding protein.

SELEX provides high affinity ligands of a target molecule. This represents a singular achievement that is unprecedented in the field of nucleic acids research. The present invention applies the SELEX procedure to the specific target of vascular endothelial growth factor (VEGF). In the Example section below, the experimental parameters used to isolate and identify the nucleic acid ligand solutions to VEGF are described.

In order to produce nucleic acids desirable for use as a pharmaceutical, it is preferred that the nucleic acid ligand 1) binds to the target in a manner capable of achieving the desired effect on the target; 2) be as small as possible to obtain the desired effect; 3) be as stable as possible; and 4) be a specific ligand to the chosen target. In most situations it is preferred that the nucleic acid ligand have the highest possible affinity to the target.

In co-pending and commonly assigned U.S. patent application Ser. No. 07/964,624, filed Oct. 21, 1992, now U.S. Pat. No. 5,496,938 ('938 patent), methods are described for obtaining improved nucleic acid ligands after SELEX has been performed. The '938 patent, entitled "Nucleic Acid Ligands to HIV-RT and HIV-1 Rev" is specifically incorporated herein by reference.

This invention includes the specific RNA ligands to VEGF shown in FIGS. 2A–F (SEQ ID NOS:4–38). The scope of the ligands covered by this invention extends to all RNA ligands of VEGF identified according to the SELEX procedure. More specifically, this invention includes nucleic acid sequences that are substantially homologous to and that have substantially the same ability to bind VEGF as the specific nucleic acid ligands shown in FIGS. 2A–F. By substantially homologous it is meant a degree of primary sequence homology in excess of 70%, most preferably in excess of 80%. Substantially the same ability to bind VEGF means that the affinity is within one order of magnitude of the affinity of the ligands described herein. It is well within the skill of those of ordinary skill in the art to determine whether a given sequence—substantially homologous to those specifically described herein—has substantially the same ability to bind VEGF.

This invention also includes the 2'-NH$_2$ modified RNA ligands to VEGF as shown in FIGS. 9A–G (SEQ ID NOS:63–146). The scope of the present invention extends, therefore, to all modified nucleic acid ligands identified according to the SELEX method as well as to all sequences that are substantially homologous to and that have substantially the same ability to bind VEGF as ligands predicted in FIGS. 9A–G.

This invention also includes additional post-SELEX modified RNA ligands having 2'-O-methyl groups on various purine residues. In addition, nucleotides that contain phosphorothioate backbone linkages were added at the 5' and 3' ends of the ligands in order to reduce or prevent degradation by exonucleases. Internal backbone positions were also identified in which phosphorothioate linkages could be substituted, without the loss of binding affinity, to reduce or prevent endonucleolytic degradation. The post-SELEX modified RNA ligands provided in Table 4 (SEQ ID NOS:147–158) demonstrate an ability to inhibit the activity of exonucleases and endonucleases, without affecting binding affinities.

Further, this invention includes ssDNA ligands to VEGF. The specific ssDNA ligands are shown in Table 8 (SEQ ID NOS:159–230).

The scope of the ligands covered by this invention extends to all ssDNA ligands of VEGF identified according to the SELEX procedure. More specifically, this invention includes nucleic acid sequences that are substantially homologous to and that have substantially the same ability to bind VEGF as the specific nucleic acid ligands shown in Table 8. By substantially homologous it is meant a degree of primary sequence homology in excess of 70%, most preferably in excess of 80%. Substantially the same ability to bind VEGF means that the affinity is within one order of magnitude of the affinity of the ligands described herein. It is well within the skill of those of ordinary skill in the art to determine whether a given sequence—substantially homologous to those specifically described herein—has substantially the same ability to bind VEGF.

This invention encompasses the use of the disclosed ligands to identify a second ligand. In one embodiment, a first SELEX identified ligand which binds to a specific site of the target molecule is used to elute secondary ligands binding to the same site. In another embodiment, a first SELEX identified ligand binding to a specific site of the target molecule is used to select secondary ligands which do not bind to the same site. In this case, SELEX is conducted in the presence of the first ligand such that the binding site is saturated with the first ligand and selection occurs for ligands binding elsewhere on the target molecule. In a further embodiment analogous to the generation of anti-idiotype antibodies, a SELEX identified ligand to VEGF may itself be used as a target molecule to identify secondary ligands resembling the VEGF binding site. Such secondary ligands may compete with VEGF-substrate binding and inhibit the biological activity of VEGF.

A review of the sequence homologies of the nucleic acid ligands of VEGF shown in FIGS. 2A–F and 9A–G and Table 8 shows that sequences with little or no primary homology may have substantially the same ability to bind VEGF. For this reasons, this invention also includes nucleic acid ligands that have substantially the same structure as the ligands presented herein and the substantially the same ability to bind VEGF as the nucleic acid ligands shown in FIGS. 2A–F and 9A–G and Table 8.

The following examples are provided to explain and illustrate the present invention and are not to be taken as limiting of the invention.

Example 1 describes the experimental procedures used to generate high-affinity nucleic acid ligands to VEGF. Example 2 describes the high-affinity RNA ligands to VEGF shown in FIGS. 2A–F. Example 3 describes the specificity of truncated RNA ligands to VEGF. Example 4 describes the experimental procedures used to generate 2'-NH$_2$ pyrimidine modified RNA ligands to VEGF. Example 5 describes post-SELEX modifications of VEGF RNA ligands with 2'-O-methyl groups on purines. Additionally, phosphorothioate backbone substitutions were made to reduce or prevent nuclease degradation without effecting binding affinity. Example 6 describes the stability of post-SELEX modified VEGF RNA ligands to ex vivo rat tissue degradation. Example 7 describes obtaining ssDNA ligands to VEGF.

EXAMPLE 1

Experimental Procedures

Materials. Recombinant human VEGF (165 amino acid form; MW 46,000) was a generous gift from Dr. Napoleone Ferrara (Genentech). All other reagents and chemicals were of the highest purity available and were purchased from commercial sources.

SELEX Essential features of the SELEX protocol have been described in detail in U.S. Pat. No. 5,270,163 as well as in previous papers from these laboratories (See, e.g., Schneider et al. (1992) J. Mol. Biol. 228:862). Briefly, DNA templates for in vitro transcription (that contain a region of thirty random positions flanked by constant sequence regions) and the corresponding PCR primers were prepared chemically using established solid phase oligonucleotide synthesis protocols.

The random region was generated by utilizing an equimolar mixture of the four unmodified nucleotides during oligonucleotide synthesis. The two constant regions were designed to contain PCR primer annealing sites, primer annealing site for cDNA synthesis, T7 RNA polymerase promoter region and restriction enzyme sites that allow cloning into vectors (FIG. 1) (SEQ ID NOS:1–3). An initial pool of RNA molecules was prepared by in vitro ascription of approximately 200 picomoles ($10^{14}$ molecules) of the double stranded DNA template utilizing T7 RNA polymerase. Transcription mixtures consisting of 100–300 nM template, 5 units/µl T7 RNA polymerase, 40 mM Tris-Cl buffer (pH 8.0) containing 12 mM MgCl$_2$, 5 mM DTT, 1 mM spermidine, 0.002% Triton X-100, 4% PEG were incubated at 37° C. for 2–3 hours. These conditions typically resulted in transcriptional amplification of 10 to 100-fold. Selections for high affinity RNA ligands were done by incubating VEGF with RNA for 10–20 minutes at 37° C. in 50 ml of phosphate buffered saline (PBS=10.1 mM Na$_1$HPO$_4$, 1.8 mM KH$_2$PO$_4$, 137 mM NaCl, 2.7 mM KCl, pH 7.4) and then separating the protein-RNA complexes from the unbound species by nitrocellulose filter partitioning (Tuerk, C. and Gold, L. (1990) Science 249:505–510). The selected RNA (which typically amounted to 5–10% of the total input RNA) was then extracted from the filters and reverse transcribed into cDNA by avian myeloblastoma virus reverse transcriptase (AMV RT). Reverse transcriptions were done at 48° C. (60 min) in 50 mM Tris buffer (pH 8.3), 60 mM NaCl, 6 mM Mg(OAc)$_2$, 10 mM DTT and 1 unit/µl AMV RT. Amplification of the cDNA by PCR under standard conditions yielded a sufficient amount of double-stranded DNA for the next round of in vitro transcription.

Nitrocellulose Filter Binding Assays. Oligonucleotides bound to proteins can be effectively separated from the unbound species by filtration through nitrocellulose membrane filters (Yarus, M. and Berg, P. (1970) Anal. Biochem. 35:450–465; Lowary, P. T. and Uhlenbeck, O. C. (1987) Nucleic Acids Res. 15:10483–10493; Tuerk, C. and Gold, L. (1990) supra). Nitrocellulose filters (0.2 µm pore size, Schleicher and Schuell, Keene, N H) were secured on a filter manifold and washed with 4–10 ml of buffer. Following incubations of $^{32}$P labeled RNA with serial dilutions of the protein for 10 min at 37° C. in buffer (PBS) containing 0.01% human serum albumin (HSA), the solutions were applied to the filters under gentle vacuum in 45 ml aliquots and washed with 5 ml of PBS. The filters were then dried under an infrared lamp and counted in a scintillation counter.

Equilibrium Dissociation Constants. In the simplest case, equilibrium binding of RNA (R) to VEGF (P) can be described by eq. 1, $$R \cdot P \overset{Kd}{\rightleftharpoons} R + P \tag{1}$$

where Kd=([R][P]/[R.P]) is the equilibrium dissociation constant Using the mass-balance equations, the fraction of bound RNA at equilibrium (q) can be expressed in terms of measurable quantities (eq. 2), $$q=(f/2Rt)\{Pt+Rt+Kd-[(Pt+Rt+Kd)^2-4PtRt]^{1/2}\} \tag{2}$$

where Pt and Rt are total protein and total RNA concentrations and f reflects the efficiency of retention of the protein-RNA complexes on nitrocellulose filters. The average value of f for VEGF in our assays was 0.7.

Most RNA ligands exhibited biphasic binding to VEGF. For those ligands, binding of RNA to VEGF is described by a model where total RNA is assumed to be partitioned between two non-interconverting components (R1 and R2)

that bind to VEGF with different affinities (eqs 3 and 4).

In this case, the fraction of total bound RNA (q) is given by eq. 5.

$$q=(f/2Rt)\{2Pt+Rt+Kd1+Kd2-[(Pt+\chi 1Rt+Kd1)^2-4Pt\chi 1Rt]^{1/2}-[(Pt+\chi 2Rt+Kd2)^2-4Pt\chi 2Rt]^{1/2}\} \quad (5)$$

where $\chi 1$ and $\chi 2(=1-c1)$ are the mole fractions of R1 and R2 and Kd1 and Kd2 are the corresponding dissociation constants.

Internally-labeled RNA ligands used for binding studies were prepared by in vitro transcription using T7 RNA polymerase (Milligan et al. (1987) Nucl. Acids Res. 15:8783) and were purified on denaturing polyacrylamide gels to ensure size homogeneity. All RNA ligands were diluted to about 1 nM in PBS, denatured at 90° C. for 2 minutes, and then cooled on ice prior to incubation with the protein. This denaturation/renaturation cycle performed at high dilution is necessary to ensure that the RNA is essentially free from dimers and other higher order aggregates. Concentrations of the stock solutions of VEGF, from which other dilutions were made, were determined from the absorbance reading at 280 nm using the calculated value for $\epsilon_{280}$ of 46,600 $M^{-1}$ $cm^{-1}$ for the VEGF dimer (Gill et al. (1989) Anal. Biochem. 182:319). Data sets that define the binding curves were fit to either eq. 2 or eq. 5 by the non-linear least squares method using the software package Kaleidagraph (Synergy Software, Reading, Pa.).

Information Boundary Determinations. High-affinity VEGF ligands were radiolabeled at the 5'-end with $\gamma$-$^{32}$P-ATP (New England Biolabs, Beverly, Mass.) and T4 polynucleotide kinase (New England Biolabs, Beverly, Mass.) for the 3'-boundary determinations, or at the 3'-end with $\alpha$-$^{32}$PCp and T4 RNA ligase (New England Biolabs) for the 5'-boundary determination. Radiolabeled RNA ligands were subjected to partial alkaline hydrolysis and then selectively bound in solution to VEGF at 5, 0.5, or 0.125 nM before being passed through nitrocellulose filters. Retained oligonucleotides were resolved on 8% denaturing polyacrylamide gels. In each experiment, the smallest radiolabeled oligonucleotide bound by VEFG at the lowest protein concentration defines the information boundary. Partial digests of the 5'- or the 3'-labelled RNA ligands with RNAse $T_1$ (Boehringer Mannheim Biochemicals, Indianapolis, Ind.) were used to mark the positions of labeled oligonucleotides ending with a guanosine.

Cloning and Sequencing. Individual members of the enriched pool were cloned into pUC18 vector and sequenced as described (Schneider, D. et al. (1992) J. Mol. Biol. 228:862–869).

Receptor Binding. VEGF was radioiodinated by the Iodegen method (Jakeman et al. (1992) J. Clin. Invest. 89:244) to a specific activity of 2.4×10$^4$ cpm/ng. Human umbilical vein endothelial cells (HUVECs) were plated in 24-well plates at a density of 1–2×10$^5$ cells/well and grown to confluence in EGM (Clonetics, San Diego, Calif.) media (24–48 hours). At confluence, the cells were washed 3 times with PBS and incubated for 2 hrs at 4° C. in $\alpha$-MEM serum-free media containing $^{125}$I-labeled VEGF with or without unlabeled competitor (VEGF, EGF, or RNA). For experiments done with RNA, 0.2 units of placental RNase inhibitor (Promega, Madison, Wis.) were included in the media It was determined that the RNA ligands were not degraded during the course of the experiment. At the end of the 2 hour incubation period, the supernatant was removed and the wells washed 2 times with PBS. HUVECs were then lysed with 1% triton X-100/1 M NaOH and the amount of cell-associated $^{125}$I-VEGF determined by gamma counting.

EXAMPLE 2

RNA Ligands to VEGF

Approximately 10$^{14}$ RNA molecules randomized at third contiguous positions (FIG. 1) (SEQ ID NO:1) were used in the initial selection targeting VEGF. Random RNA bound to VEGF with an affinity of approximately 0.2 $\mu$M. After 13 rounds of SELEX, the observed improvement in affinity of the evolved RNA pool was about two orders of magnitude (data not shown). 64 isolates were cloned and sequenced from this evolved pool, and 37 unique sequences found (sequences differing at only one or two positions were not considered unique). 34 of the 37 unique sequences could be classified into six families based on sequence similarity in the evolved region (FIGS. 2A–F) (SEQ ID NOS:4–38). The evolved sequence is provided in capitol letters in FIG. 2. Lower case letters indicate portions of the fixed sequence included in the alignment. The cloned sequence included both the evolved and fixed sequences. Three unique clones, 4 (GGGAUGUUUGGCUAUCUCGGAUAGUGCCCC) (SEQ ID NO:39), 16 (GCUUAAUACGACUCACUNUA-GGGAGCUCAG)(SEQ ID NO:40) and 18 (UUGAGUGAUGUGCUUGACGUAUCGCUGCAC) (SEQ ID NO:41) had a more limited sequence similarity with members of the six families.

Consensus Structures. In addition to allowing determination of consensus primary structures, groups of similar sequences consisting of members that share a defined functional property often contain useful clues for secondary structure prediction (James et al. (1989) Meth. Enzymol. 180:227). The underlying assumption is that ligands with similar primary structures are capable of adopting similar secondary structures in which the conserved residues are organized in unique, well-defined motifs. In this context, ligands which have strong, unambiguous secondary structures can provide good structural leads for other sequences within a similar set where consensus folding may be less obvious. Conserved elements of secondary structure, such as base-pairing, may also be detected through covariation analysis of aligned sequence sets (James et al. (1989) supra; Gutell et al. (1992) Nucl. Acids Res. 20:5785). The predicted consensus secondary structures for the six sequence families are shown in FIGS. 3A–F (SEQ ID NOS:42–47).

The most highly conserved residues in the family 1 sequence set (A17, G19 and the CAUC sequence at positions 23–26) can be accommodated in the 9–10 nucleotide loop (SEQ ID NO:42). Base-pairing covariation between positions 16 and 27 (G-C occurs with a frequency of 8 out of 11 times (8/11) and C-G with a frequency of 3/11), positions 15 and 28 (U-G, 7/1 1; G-C, 3/1 1; U-A, 1/11) and positions 14 and 29 (G-C, 511 1; U-A, 21 1, and C-G, 1/11) supports the predicted secondary structure. It is worth noting that many ligands in this family have stable extended stems that contain up to 15 base pairs.

In the family 2 sequence set, the strongly conserved UGCCG and UUGAUG(G/U)G sequences (positions 8–12 and 26–33) are circularly permutated. In the consensus secondary structures, these nucleotides are found in an identical arrangement within or adjacent to the asymmetrical internal loop (FIG. 3A) (SEQ ID NO:43). This result suggests that the nucleotides outside of the consensus motif shown in FIGS. 3A–F are unimportant for binding. Base-pairing covariation is noted between positions 5 and 36 (C-G, 2/7; G-C, 2/7; U-A, 1/7; G-U, 1/7), 6 and 35 (A-U, 4/7; C-G, 1/7; G-C, 1/7), 7 and 34 (A-U, 4/7; G-C, 1/7), 11 and 28 (C-G, 6/7; G-C, 1/7), 12 and 27 (G-U, 6/7; C-G, 1/7), 13 and 26 (A-U, 5/7; G-C, 1/7; G-U, 1/7), 14 and 25 (G-C, 4/7; C-G, 2/7) and 15 and 24 (C-G, 4/7; G-C, 217).

Family 3 and family 4 sequence sets are characterized by highly conserved contiguous stretches of 21 (GGGAACCUGCGU(C/U)UCGGCACC (SEQ ID NO:48), positions 11–31) and 15 (GGUUGAGUCUGUCCC (SEQ ID NO:49), positions 15–29) arranged in bulged hairpin motifs (FIGS. 3C and D) (SEQ ID NOS:44–45). Base-pairing covariation is detected in family 3 between positions 8 and 33 (A-U, 2/4; G-C, 2/4), 9 and 32 (A-U, 2/4; U-A, 1/4; G-C, 1/4), and 10 and 31 (A-U, 1/4; G-C, 3/4) and in family 4 between positions 13 and 31 (A-U, 4/7; C-G, 2/7; U-A, 1/7) and 14 and 30 (C-G, 3/7; U-A, 3/7; A-U, 1/7).

Family 5 consensus secondary structure is an asymmetrical internal loop where the conserved UAGUUGG (positions 9–15) and CCG (positions 29–31) sequences are interrupted by less conserved sequences (FIG. 3E) (SEQ ID NO:46). Modest base-pairing covariation is found between positions 8 and 32 (A-U, 2/4; U-G, 1/4), 16 and 26 (G-C, 2/4; A-U, 1/4), 17 and 25 (A-U, 2/4; G-C, 1/4) and 18 and 24 (C-G, 2/4; G-C, 1/4).

Family 6 has only two sequences and therefore the concept of consensus sequence or consensus structure is less meaningful. Nevertheless, the two sequences are very similar (90% identity) and can be folded into a common motif (FIG. 3F) (SEQ ID NO:47). Base-pairing covariation is found between positions 1 and 32 (A-U, 112; G-U, 1/2), 2 and 31 (C-G, 1/2; G-C, 1/2), 14 and 20 (U-A, 1J2; G-C, 1/2) and 15 and 19 (A-U, 1/2; G-U, 1/2).

Affinities. The affinity of all unique sequence clones for VEGF was screened by determining the amount of RNA bound to VEGF at two protein concentrations (1 and 10 nM). Binding of the best ligands from each of the six sequence families was then analyzed over a range of protein concentrations (FIGS. 4A–F). Dissociation constants were calculated by fitting the data points to either eq. 2 (monophasic binding) or eq. 5 (biphasic binding) and their values are shown in Table 1.

Figure 5A:
Figure 5B:
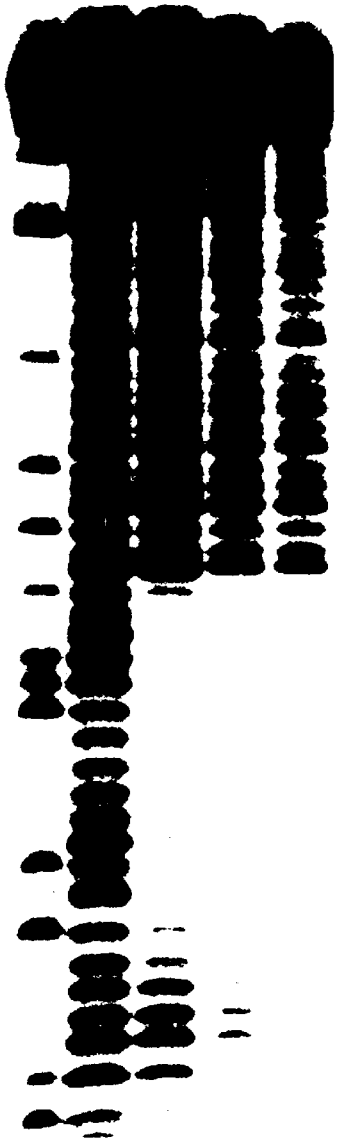

Information Boundaries. In order to determine the minimal sequence information necessary for high-affinity binding to VEGF, deletion analyses were performed with representative members from each of the six families. These experiments were done by radiolabeling RNA ligands at either the 3' end or the 5' end (for the 3' or the 5' boundary determinations, respectively) followed by limited alkaline hydrolysis, partitioning of the free and the bound RNA by nitrocellulose filtration and resolving the hydrolytic fragments that retained high affinity for VEGF on denaturing polyacrylamide gels (Tuerk et al. (1990) J. Mol. Biol. 213:749). The combined information from the 3' and the 5' boundary experiments outlines the shortest sequence segment that has high affinity for the protein (FIG. 5) (SEQ ID NO:50). It is important to realize that these experiments define boundaries sequentially at the unlabeled ends of ligands in the context of full-length labeled ends. Since the full-length ends may provide additional contacts with the protein or participate in competing secondary structures, ligands truncated at both ends may have lower or higher affinities for the protein than their full-length parent. The following truncated ligands were prepared by in vitro transcription from synthetic DNA templates: 100t (Family 1) GGCCGGUAGUCGCAUGGCCCAUCGCGCCCGG (SEQ ID NO:51), 44t (Family 2) GGaaGCUUGAU-GGGUGACACACGUCAUGCCGAGCu (SEQ ID NO:52), 12t (Family 3) GGAAGGGAACCUGCGUCUCGGCAC-Cuucg (SEQ ID NO:53), 40t (Family 4) GGUCAACGG-UUGAGUCUGUCCCGuucgac (SEQ ID NO:54), 84t (Family 5) GgcucaaUAGUUGGAGGCCUGUCCUCGCC-GUAGAGC (SEQ ID NO:55) and 126t (Family 6) GGaACGGUUCUGUGUGUGGACUAGCCGCGGCCGuu (SEQ ID NO:56) (letter t designates truncated sequences; underlined guanines are not present in the original sequences and were added to increase the transcriptional efficiency (Milligan et al. (1990) supra); lowercase letters indicate nucleotides from the constant sequence region). Binding curves for these truncated ligands and their dissociation constants are shown alongside their parent ligands in FIGS. 4A–F and Table 1. The dissociation constants of the truncated versus full-length ligands are generally comparable, although ligands 40t (SEQ ID NO:54) and 126t (SEQ ID NO:56) clearly bind to VEGF significantly less well than the corresponding full-length ligands.

Competition experiments revealed that binding of all possible pairwise combinations of truncated ligands representing each of the families is mutually exclusive (lot, 44t, 12t, 40t, 84t and 126t (SEQ ID NOS:51–56, respectively). Furthermore, all of these ligands are displaced by low-molecular weight (≅5,100 Da) heparin (data not shown). Truncated ligands and low-molecular weight heparin were used in these studies in order to maximize the probability of observing non-competing ligand pairs. It appears, therefore, that although there are multiple non-isomorphic solutions to high-affinity binding to VEGF, all examined ligands may bind to the same region of the protein. Proteins in general may have "immunodominant" domains for nucleic acid ligands.

EXAMPLE 3

Specificity of Truncated RNA Ligands to VEGF

Binding of two truncated high-affinity ligands, 100t and 44t (SEQ ID NOS:51–52), to four other heparin binding proteins (bFGF, PDGF, antithrombin III and thrombin) was tested in order to address the question of specificity. Dissociation constants were determined using the nitrocellulose filter partitioning technique. Results are shown in Table 2. Binding of these ligands to VEGF in a buffer containing 10 mM dithiothreitol is at least 1000-fold weaker.

Figure 6:
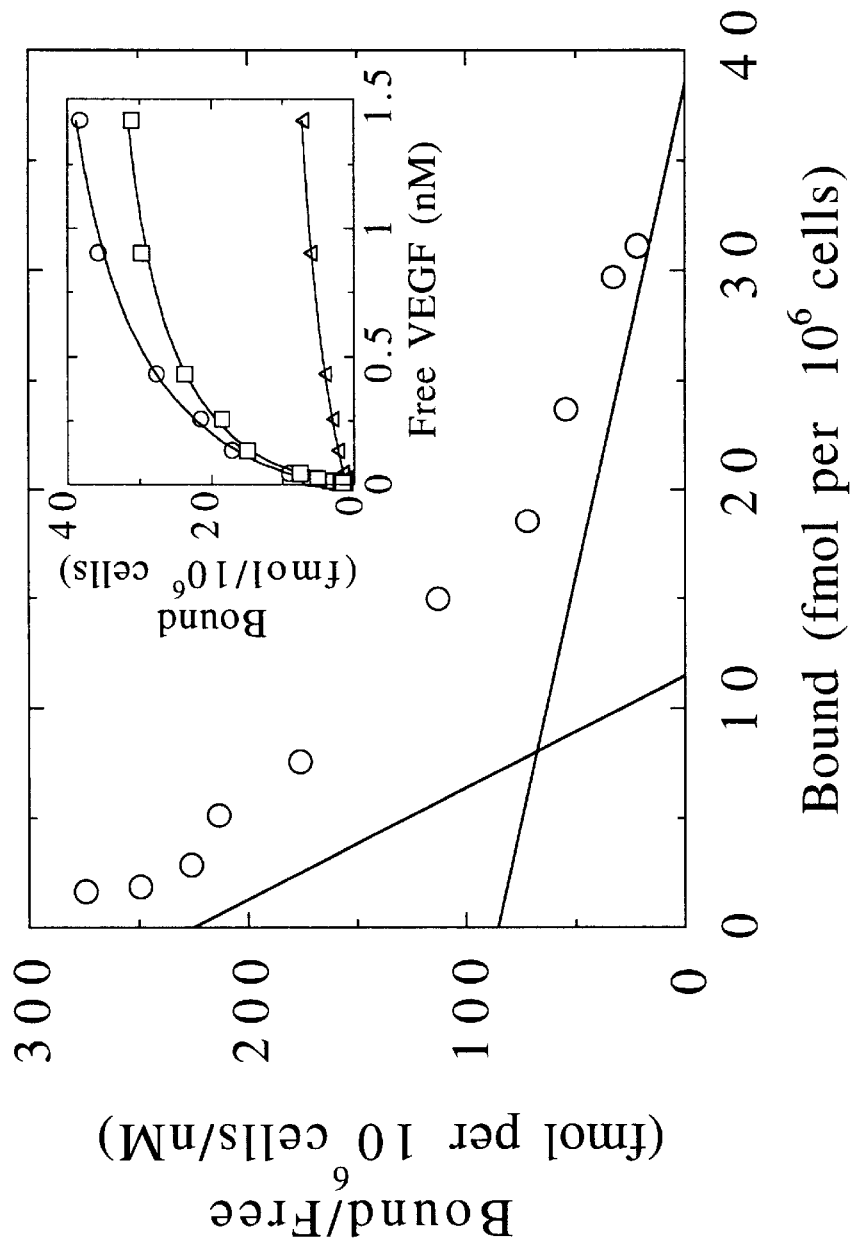
FIG. 6 shows the Scotchard analysis of $^{125}$I-VEGF binding to HUVECS. Data points are averages of two determinations. Increasing concentrations of $^{125}$I-VEGF were incubated with $2 \times 10^5$ cells in the presence or absence of 50-fold excess of unlabeled VEGF to determine the amount of total (○), specific (□) and non-specific (Δ) binding of $^{125}$I-VEGF as a function of free $^{125}$I-VEGF concentration (insert).

Receptor Binding. Unlabeled VEGF but not EGF was shown to inhibit binding of $^{125}$I-VEGF to HUVECs in a concentration-dependent manner (data not shown), confirming that $^{125}$I-VEGF binds to specific sites on HUVECs. As previous studies have reported (Myoken et al. (1991) Proc. Natl. Acad. Sci. USA 88:5819), two classes of receptors on HUVECs were observed to bind VEGF with dissociation constants of ~5×10⁻¹¹ M (7,000 receptors/cell) and ~5×10⁻ M (20,000 receptors/cell) (FIG. 6).

Figure 7:
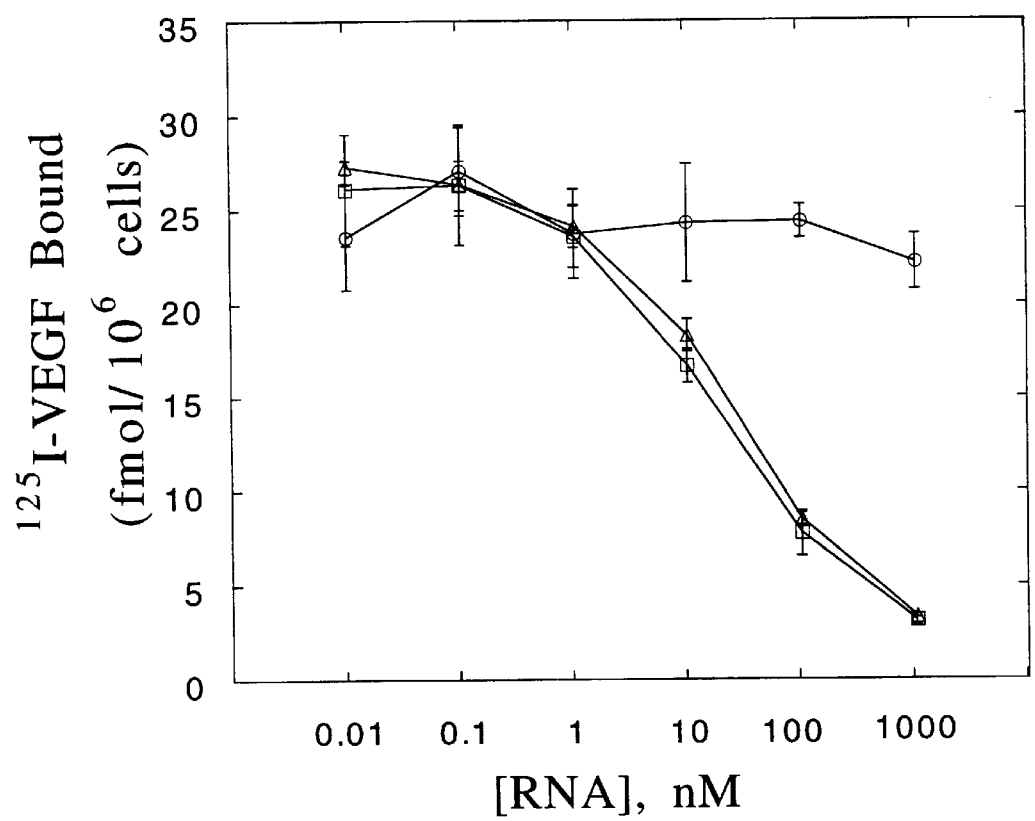
FIG. 7 shows the effect of random RNA (○) and representative high affinity RNA ligands loot (SEQ ID NO:51) (family 1) (Δ) and 44t (SEQ ID NO:52) (family 2) (□) on binding of $^{125}$-VEGF to cell-surface receptors as a function of RNA concentration. The inhibitory affect of high affinity ligands representing other sequence families is virtually identical to that of ligands 100t and 44t.

A group of truncated RNA ligands representing each of the sequence families (l00t, family 1; 44t, family 2; 12t, family 3; 40t, family 4; 84t, family 5; and 126t, family 6 (SEQ ID NOS:51–56)), as well as random RNA were tested for their ability to inhibit binding of VEGF to its cell-surface receptors. All high-affinity ligands, but not random RNA, inhibited VEGF-VEGF receptor interaction in a concentration-dependent manner with half-inhibition occurring in the 20–40 nM range (FIG. 7).

EXAMPLE 4

Modified 2'-NH$_2$ Pyrimidine RNA Ligands to VEGF

In order to generate ligands with improved stability in vivo, two SELEX experiments (A and B) targeting VEGF were initiated with separate pools of randomized RNA containing amino (NH$_2$) functionalities at the 2'-position of each pyrimidine. Starting ligand pools for the two experiments contained approximately 10$^{14}$ molecules (500 pmols) of modified RNA randomized at 30 (SELEX experiment A) and 50 (SELEX experiment B) contiguous positions. The starting RNAs and the corresponding PCR primers are defined in FIG. 8 (SEQ ID NOS:57–62). Sequences corresponding to the evolved regions of modified RNA are shown in FIGS. 9A–G.

Ligands with similar primary structures were grouped into 5 families and their consensus sequences are shown below each sequence set FIGS. 9A–G (SEQ ID NOS:63–146). Groups of sequences with similar primary structure (families) have been aligned in FIGS. 9A–G and their consensus sequences are shown below each set Pairs of similar/related sequences, sequences that could not be included in any of the families ("other sequences") and sequences that correspond to ligands that bind additionally to nitrocellulose filters with high affinity have been shown in separate groups. Letter N in a sequence indicates an ambiguous position on a sequencing gel. Italicized letter N in a consensus sequence indicates a position that is not conserved (i.e., any nucleotide may be found at that position). Dissociation constants for Random RNA A (30N8), Random RNA B (50N7) and a set of modified (2'-amino pyrimidine high-affinity RNA ligands for VEGF are shown in Table 3.

EXAMPLE 5

Post SELEX Modifications of VEGF RNA Ligands

In an attempt to further stabilize the nucleic acid ligands of the invention, certain post-SELEX modifications were done. The ligand NX107 (SEQ ID NO:147) was chosen as a model for post-SELEX modification. NX107 is a truncated version of Ligand 24A (SEQ ID NO:79) from Example 4. All of the pyrimidines in NX107 have an NH$_2$ group substituted at the 2'-position of the ribose. This example describes substitution of O-Methyl groups at the 2'-position of the ribose of certain of the purines of NX107. Additionally, phosphorothioate nucleotides were added at the 5' and 3' ends of the ligands and in at least one instance, at an internal position. The various substitutions to the ligand were designed to inhibit the activity of exonucleases and endonucleases, but not affect binding affinity.

To this end, certain ligands were synthesized and tested for binding affinity. The sequences and the results of the binding studies are provided in Table 4. The binding studies were performed using the protocols described in Example 1.

EXAMPLE 6

Stability of Post-SELEX Modified VEGF Ligands to Ex Vivo Rat Tissue Degradation

In order to be able to quickly assess the effects of ligand modifications on stability to tissue nucleases, the following assay was developed. Brain, kidney, liver and spleen tissues were removed from a freshly sacrificed rat, washed in saline to remove blood, and sliced into approximately 10 mm$^3$ pieces. Each piece was put into an Eppendorf tube with 50 µl PBS and quick frozen on dry ice. Tissues from the same rat were used for all the experiments described here. The ligand to be tested was 5'end-labeled with $^{32}$P, added to the thawed tissue slice in 80 µl PBS, and incubated at 37° C. Aliquots were withdrawn at 3, 10, 30, and 60 minutes, added to an equal volume of formamide dyes on ice, and quick-frozen on dry ice. The samples were run on a 20% denaturing acrylamide gel along with equal counts of the unincubated ligand, and a partial alkaline hydrolysate of the ligand (or a related ligand) for sequence markers. The gels were dried and exposed to X-ray film and a phosphorimager plate (for quantitation of degradation).

The VEGF ligands used in this study are shown in Table 4. Each ligand has the same core 24-mer sequence derived from a truncated 2'NH$_2$-pyrimidine SELEXed ligand (NX-107)(SEQ ID NO:147). NX-178 (SEQ ID NO:149) is the same 2'amino pyrimidine ligand with phosphorothioate backbone linked thymidine caps at the 5'- and 3'-ends of the ligand. NX-190 (SEQ ID NO:150) is an all DNA version of the same sequence with the above-described caps, and NX-191 (SEQ ID NO:151) is an all 2'OMe version. NX-213 (SEQ ID NO:152) is the capped amino ligand with all the purines 2'OMe substituted except four. NX-2 15 (SEQ ID NO:154) is the same as NX-213 with an internal phosphorothioate linkage between A7 and U8.

Tables 5 and 6 provide the results obtained by this assay on rat brain and kidney tissues as indicated by the percent of full length material found at the various time points. For this analysis, a ligand is still considered functionally intact with cuts in the phosphorothioate caps. The other tissues assayed had similar results. The post-SELEX modifications were successful in protecting the ligand from various endo- and exonucleases.

EXAMPLE 7

SSDNA Ligands to VEGF

This example demonstrates the ability to obtain ssDNA ligands to vascular endothelial growth factor (VEGF).

Most of the materials and methods are the same as those described in Example 1. Two libraries of synthetic DNA oligonucleotides containing 40 random nucleotides flanked by invariant primer annealing sites were amplified by the Polymerase Chain Reaction (CR) using oligonucleotide primers as shown in Table 7 (SEQ ID NOS:237–242). The protocols for the SELEX procedure are as described by Jellinek et al. (PNAS (1993) 90:11227–11231), in the SELEX Patent Applications and in Example 1. VEGF protein binding assays, receptor binding assays, and information boundary determinations are also described in Example 1.

The ssDNA ligands identified are shown in Table 8 (SEQ ID NOS:159–220). Only the sequence of the evolved region is provided in Table 8, however, each of the clones also includes the fixed regions of either SEQ ID NO:237 or SEQ ID NO:240. Clones named with numbers only include the fixed regions of SEQ ID NO:237 and clones named with b and number included the fixed regions of SEQ ID NO:240. Truncations (information boundary determinations) were performed on a number of ligands, which is also provided in Table 8 (SEQ ID NOS:221–230). Four sequence families were obtained from the alignment of the primary sequences of these ligands and a consensus sequence generated for each family (SEQ ID NOS:231–236). Orphan sequences were also identified. Select ligands were tested in the VEGF protein binding assay with results being shown in Table 8. The starting DNA random pool had a binding affinity Kd of approximately 200 nM. In the VEGF receptor binding assay, the truncated clone 33t (SEQ ID NO:224) had a Ki of 3 nM.

TABLE 1

Dissociation Constants For a Representative Set of Full-Length and Truncated High-Affinity RNA Ligands for VEGF.[a]

| LIGAND[b] | Kd1 (nM)[c] | $\chi^{1\,d}$ | Kd2 (nM)[e] | SEQ ID NOS. |
|---|---|---|---|---|
| 100 | 0.20 ± 0.02 | 0.82 ± 0.02 | 42 ± 30 | 11 |
| 100t | 0.42 ± 0.04 | 0.76 ± 0.03 | 182 ± 94 | 51 |
| 44 | 1.7 ± 0.5 | 0.70 ± 0.11 | 38 ± 32 | 20 |
| 44t | 0.48 ± 0.04 | 0.73 ± 0.01 | 82 ± 23 | 52 |
| 12 | 0.48 ± 0.07 | 0.56 ± 0.03 | 21 ± 5 | 22 |
| 12t | 1.1 ± 0.2 | 0.78 ± 0.04 | 180 ± 160 | 53 |
| 40 | 0.19 ± 0.09 | 0.19 ± 0.04 | 10 ± 1 | 28 |
| 40t[f] | 20 ± 1 | — | — | 54 |
| 84 | 0.82 ± 0.2 | 0.45 ± 0.06 | 21 ± 5 | 36 |
| 84t | 1.8 ± 0.4 | 0.53 ± 0.07 | 31 ± 10 | 55 |
| 126 | 0.14 ± 0.04 | 0.40 ± 0.04 | 11 ± 3 | 38 |
| 126t | 1.4 ± 0.2 | 0.54 ± 0.03 | 181 ± 57 | 56 |

[a]Binding experiments were done as described in Example 2 and errors are given as standard deviations. [b]Full length, and truncated ligands are listed in pairs and represent sequence families 1–6, in order. [c]Dissociation constant of the higher-affinity binding component as defined in eq. 5. [d]Mole fraction of the high-affinity binding component as defined in eq. 5. [e]Dissociation constant of the lower-affinity binding component as defined in eq. 5. [d]Mole fraction of the high-affinity binding component as defined in eq. 5. [e]Dissociation constant of the lower-affinity binding component as defined in eq. 5. [f]Dissociation constant for ligand 40t was determined by fitting the data points to eq. 2.

TABLE 2

Binding of 100t and 44t Truncates

| Target Molecule | 100t (Kd) (SEQ ID. NO. 51) | 44t (Kd) (SEQ ID. NO. 52) |
|---|---|---|
| bFGF | 1 μM | 0.6 μM |
| PDGF | 0.6 μM | 0.6 μM |
| antithrombin III | 3 μM | 12 μM |
| thrombin | >10 μM | >10 μM |
| plasminogen activator inhibitor I | >10 μM | >10 μM |

TABLE 3

| Ligand | Kd1, nM | $\chi^1$ | Kd2, nM | SEQ ID NOS. |
|---|---|---|---|---|
| Rndm RNA A | 83 ± 21 | — | — | |
| Rndm RNA B | 240 ± 140 | — | — | |
| 14A | 0.70 ± 0.16 | 0.42 ± 0.05 | ≈$10^2$ | 76 |
| 23A | 2.8 ± 0.3 | — | — | 78 |
| 24A | 0.71 ± 0.14 | 0.79 ± 0.5 | ≈$10^2$ | 79 |
| 41A | 0.86 ± 0.19 | 0.68 ± 0.11 | ≈$10^2$ | 93 |
| 17B | 0.028 ± 0.008 | 0.62 ± 0.05 | ≈$10^2$ | 65 |
| 26B | 0.37 ± 0.10 | 0.74 ± 0.15 | ≈$10^2$ | 82 |
| 30B | 0.034 ± 0.009 | 0.77 ± 0.06 | $10^1$–$10^2$ | 68 |
| 32B | 0.050 ± 0.023 | 0.50 ± 0.06 | 15 ± 9 | 104 |
| 34B | 0.068 ± 0.016 | 0.82 ± 0.06 | $10^1$–$10^2$ | 70 |
| 44B | 0.14 ± 0.06 | 0.54 ± 0.09 | 9 ± 6 | 95 |

TABLE 4

| SEQ ID NO: | Ligand | SEQUENCE | | | VEGF Protein Binding Kd | VEGF Receptor Binding Ki |
|---|---|---|---|---|---|---|
| 147 | NX-107 | | A̲C̲C̲ C̲U̲G̲ A̲U̲G̲ G̲U̲A̲ G̲A̲C̲ G̲C̲C̲ GGG G̲U̲G̲ | | | 1 nM |
| 148 | NX-176 | | A̲C̲C̲ C̲U̲G̲ A̲U̲G̲ G̲U̲A̲ G̲A̲C̲ G̲C̲C̲ GGG G̲U̲G̲ | | 65 nM | 10 nM |
| 149 | NX-178 | T*T*T*T* | A̲C̲C̲ C̲U̲G̲ A̲U̲G̲ G̲U̲A̲ G̲A̲C̲ G̲C̲C̲ GGG G̲U̲G̲ | T*T*T*T*T | 0.7 nM | 1 nM |
| 150 | NX-190 | T*T*T*T* | ACC CTG ATG GTA GAC GTT GGG GTG | T*T*T*T*T | | |
| 151 | NX-191 | T*T*T*T* | ACC CUG AUG GUA GAC GCC GGG GUG | T*T*T*T*T | 120 nM | 500 nM |
| 152 | NX-213 | T*T*T*T* | A̲C̲C̲ C̲U̲G̲ A̲U̲G̲ G̲U̲A̲ G̲A̲C̲ G̲C̲C̲ GGG G̲U̲G̲ | T*T*T*T*T | 0.2 nM | 1 nM |
| 153 | NX-214 | T*T*T*T* | A̲C̲C̲ C̲U̲G̲ A̲U̲G̲ G̲U̲A̲ G̲A̲C̲ G̲C̲C̲ GGG G̲U̲G̲ | T*T*T*T*T | 0.2 nM | 1 nM |
| 154 | NX-215 | T*T*T*T* | A̲C̲C̲ C̲U̲G̲ A*U̲G̲ G̲U̲A̲ G̲A̲C̲ G̲C̲C̲ GGG G̲U̲G̲ | T*T*T*T*T | 0.2 nM | 1 nM |
| 155 | NX-203 | | A̲C̲C̲ C̲U̲G̲ A̲U̲G̲ G̲U̲A̲ G̲A̲C̲ G̲C̲C̲ GGG G̲U̲G̲ | | | |
| 156 | NX-204 | | A̲C̲C̲ C̲U̲G̲ A̲U̲G̲ G̲U̲A̲ G̲A̲C̲ G̲C̲C̲ G̲G̲G̲ G̲U̲G̲ | | | |
| 157 | NX-205 | | A̲C̲C̲ C̲U̲G̲ A̲U̲G̲ G̲U̲A̲ G̲A̲C̲ G̲C̲C̲ G̲G̲G̲ G̲U̲G̲ | | | |
| 158 | NX-206 | | A̲C̲C̲ C̲U̲G̲ A̲U̲G̲ G̲U̲A̲ G̲A̲C̲ G̲C̲C̲ GGG G̲U̲G̲ | | | |

N = 2'OH  
N̲ = 2'NH₂  
N = 2'OMe  
N* = phosphorothioate  
*N* = 2'deoxy  
N̲ = 2'OMe:2'OH::2:1

TABLE 5

EX VIVO RAT TISSUE STABILITY: BRAIN PERCENT FULL LENGTH

| TIME (min.) | NX 107 | NX 178 | NX 190 | NX 191 | NX 213 |
|---|---|---|---|---|---|
| 3 | 94.82 | 100.48 | 99.61 | 98.09 | 100.33 |
| 10 | 91.66 | 96.27 | 99.23 | 97.75 | 99.81 |
| 30 | 79.47 | 86.98 | 97.53 | 96.54 | 99.00 |
| 60 | 73.04 | 79.39 | 96.37 | 95.45 | 99.02 |

TABLE 6

EX VIVO RAT TISSUE STABILITY: KIDNEY PER CENT FULL LENGTH

| TIME (min.) | NX 107 | NX 178 | NX 190 | NX 191 | NX 213 |
|---|---|---|---|---|---|
| 3 | 90.34 | 96.07 | 99.05 | 97.07 | 100.01 |
| 10 | 69.97 | 96.55 | 97.13 | 97.76 | 100.13 |
| 30 | 46.30 | 92.37 | 94.56 | 98.53 | 99.40 |
| 60 | 45.00 | 90.14 | 91.83 | 97.75 | 99.09 |

TABLE 7

Starting Single Stranded DNAs and the Corresponding PCR Primers Used in the ssDNA SELEX Experiments Targeting VEGF

SELEX experiment A

```
Starting ssDNA:
5'-ATCCGCCTGATTAGCGATACT(40N)ACTTGAGCAAAATCACCTGCAGGGG-3'     (SEQ ID NO: 237)
PCR Primer 1:
5'-JJJCCCCTGCAGGTGATTTTGCTCAAGT-3'                            (SEQ ID NO: 238)
PCR Primer 2:
5'-ATCCGCCTGATTAGCGATACT-3'                                    (SEQ ID NO: 239)
```

SELEX Experiment B

```
Starting ssDNA:
5'-CTACCTACGATCTGACTAGC(40N)GCTTACTCTCATGTAGTTCCT-3'          (SEQ ID NO: 240)
PCR Primer 1:
5'-AJAJAGGAACTACATGAGAGTAAGC-3'                                (SEQ ID NO: 241)
PCR Primer 2:
5'-CTACCTACGATCTGACTAGC-3'                                     (SEQ ID NO: 242)
```

J = biotin (from biotin phosphoramidite (e.g., Glen Research, Sterling, VA)

TABLE 8

VEGF ssDNA ligands
ssDNA bulk pool, BH SELEX:0.44 nM

| SEQ ID NO: | ligand | | Kd, nM |
|---|---|---|---|
| | Family 1 | | |
| 159 | 3 | acaacggcgtggaagactagagtgcagccgaacgcatcta | |
| 160 | 5 | acgctacaagtccgctgtggtagacaagagtgcaggcaag | |
| 161 | 9 (3x) | aggcccgtcgaagntagagcgcagggccccaaaataccg | |
| 162 | 10 | gtaccatccacggtttacgtggacaagagggccctggtac | 1 |
| 163 | 11 | tcactacaagtccgccgtggtagacaagagtgcaggcaag | |
| 164 | 15 | accgctgtgtagttccttaggactagagggccgcctac | 0.88 |
| 165 | 21 | taggcttgacgtcttctgactagagtgcagtcaaaccc | |
| 166 | 27 | tgcaggtcgactctagaggatccccgggtaccgagctcga | |
| 167 | 31 | acggtttacgtggacaagagggccctggtac | |
| 168 | 32 (3x) | ggtggactagaggncagcaaacgatccttggttcgcgtcc | 2 |
| 169 | 33 | tcaagcactcccgtcttccagacaagagtgcagggcctct | 2 |
| 170 | 35 | cgtgatggacaagagggccctatccaccggatatccgtc | |
| 171 | 37 | caagcagtgcccgtcttccagacaagagtgcaggcctct | |
| 172 | 39 | tgatccaccgtttatagtccgtggtagacaagagtgcagg | |
| 173 | 41 | aacacacaagaggacagttacaggtaacatccgctcagg | |
| 174 | 49 | agtggcgtctatagacaagagtgcagcccgagtttca | |
| 175 | 50 | ccacaagagggcagcaagtg-tacaactacagcgtccgg | |
| 176 | b56(8x) | gcagggccacgtctattagactagagtgcagtggttc | 0.5 |
| 177 | b69 | acggtccaaaggtttcccatccgtggactagagggcacgtgctta | |
| 178 | b80 | ccgtcgcgtgactataaccacacgcagactagagtgcagggctta | 8.1 |
| 179 | b81** | ccgaatggggctgcgactgcagtggacgtcacgtcgtta | 0.3 |
| 180 | b91** | acgcaagagagtcnccgaatgcagtctcagccgctaaca | |
| 231 | Consensus | agacaagagtgcagg | |
| 232 | | ggactagagggcagt | |

TABLE 8-continued

VEGF ssDNA ligands
ssDNA bulk pool, BH SELEX:0.44 nM

| SEQ ID NO: | ligand | | Kd PCR |
|---|---|---|---|
| | Family 2 | | |
| 181 | 2 | cannncactgcaagcaattgtggcccaaagggctgagt | |
| 182 | 14 | gctcgcttacaaaagggagccactgtagcccagactggac | |
| 183 | 25 (2x) | ggttatggtgtggttccgaatggtgggcaaagtaacgctt | |
| 184 | 40 | gcttgngctccgaaggggcgcgtatccaaggacggttc | |
| 185 | 46 | tatggagtggttccgaatggtgggcaaagtaacgctt | |
| 186 | b54 | tgcnngcgggcggttctccggatgggaccataaggctttagctta | 2.5 |
| 187 | b55 | acaaggggtcctgnngaatggggggaatacgctagccgaa | 15 |
| 188 | b59 | aacacgagcatgtggggtcccttccgaatggggggtacaggctta | 91 |
| 189 | b79 | gaggcattaggtccgaatggtagtaatgctgtcgtgccttgctta | 2 |
| 190 | b81** | ccgaatgggctgcgactgcagtggacgtcacgtcgtta | 0.3 |
| 191 | b85 | gaggaggtgcgttgtccgaaggggtcgttagtcacctcgtgctta | .15 |
| 192 | b88 (5x) | gcaaggggtcctgccgaatgggggaatacgctagccgaaa | 34 |
| 193 | b89 (3x) | atccttccgaatgggggaaatggcgnccca | 2–3 |
| 194 | b91** | acgcaagagaggtcnccgaatggcagtctcagccgctaaca | 3.9 |
| 195 | b99 | cacgataatcctccgaaagcgttgtccgaatgggtcgttagctta | 34 |
| | Consensus | ctccgaatgggggnaaa g | |
| | Family 3 | | |
| 196 | 18 | tatcaccccactggatagagccgcagcgtgccctact | |
| 197 | 19 | gcccactgcatagagggacggttgtttccgccggtgttt | |
| 198 | b51 | gtgaaggagccccaactggatagaagccttaaggcggtgt | |
| 199 | b60 | ccaccgcagagtgttacaccccataggagaagtccggatggctta | 26 |
| 200 | b62 | ccactgcatagagagtcgcaagacacggtgctttattcnccgctta | 2.9 |
| 201 | b63 | tgccccactggatagagtaggaggcctagccgacacggtgctta | |
| 202 | b65 | cgaggtcccccactggatagagttgttgaaacaacggtgcgctta | 0.53 |
| 203 | b66 | aacacttcccccactggatagaggcctttcgcagagccggtgctta | 1.3 |
| 204 | b95 | ccactgcatagagaactggatcgacggtccaaagttcggtgctta | 0.9 |
| 205 | b96 | ccactgcatagagatactggattcgacnnnccaaagtttcggtgctta | 1.5 |
| 206 | b97 | ccactgcagagagtcaaccttacgangccaaggttgcggtgctta | >1 |
| 234 | Consensus | ccccactggatagag | |
| 235 | | ccccactgcatagag | |
| | Family 4 | | |
| 207 | 1 | tctgcgagagacctactggaacgttttgtgatattcaca | 12 |
| 208 | 6 | atacacccggcgggcctaccggatcgttgatttctctcc | 1.0 |
| 209 | 13 | acgcccctgagacctaccggaatnttntcgctcgctaggccta | |
| 210 | 23 | gggcatctaacccagacctaccggaacgttatcgcttgtg | 0.75 |
| 211 | 44 | ggtgtgaaccagacctacnggaacgttatcgcttgtg | 0.4 |
| 236 | Consensus | agacctaccggaacgtt | |
| | Orphans | | |
| 212 | 4 | catcagtattatataacgggaaccaacggcaaatgctgac | |
| 213 | 7 | tccnnggggagaatagggttagtcggagaagttaatcgct | |
| 214 | 16 | cgggaacgtgtggttacncggcctactggattgtttcctg | |
| 215 | 30 | ggtaggtccggtgtgaaagaggttcgcatcaggta | |
| 216 | 38 | cctcaggcaacatagttgagcatcgtatcgatcctggag | |
| 217 | 43 | ttggcttgagtcccgggacgcactgttgacagtggagt | |
| 218 | 45 | cagcaggttagtataacgggaaccaacggcaaatgctgac | |
| 219 | b53 | gcaaggggcatctccggaatcggttaatctgacttgcaatacgctta | 2.5 |
| 220 | b98 | gatccacgaagaagcttactctcatgtagttcca | >100 |
| | Truncates | | |
| 221 | 10t | gtaccatccacggtttacgtggacaagagggccctggtac | 5 |
| 222 | 15t | gtagttcctttaggactagagggccgcctac | 3 |
| 223 | 32t | tggactagaggncagcaaacgatccttggttcgcgtcc | 17 |
| 224 | 33t | cccgtcttccagacaagagtgcaggg | 0.7 |
| 225b | 56t | agggccacgtctatttagactagttagtgcagtggttc | 0.2 |
| 226b | 85t | ggaggtgcgttgtccgaaggggtcgagtcacctc | 0.3 |
| 227 | 88t | gcaaggggtcctgccgaatgggggaatacgctagccgaaa | 19 |
| 228b | 65t | cgaggtcccccactggatagagttgttgaaacaacggtgcgctta | 0.32 |
| 229b | 66t | aacacttcccccactggatagaggcctttcgcagagccggtgctta | 0.35 |
| 230b | 23t | gggcatctaacccagacctaccggaacgttatcgcttgtg | >200 |

What is claimed is:

1. A method of inhibiting binding of vascular endothelial growth factor (VEGF) to its receptor, comprising:
   a) providing a nucleic acid ligand to VEGF; and
   b) contacting the nucleic acid ligand with said VEGF under conditions where a VEGF:nucleic acid binding pair is formed, whereby binding of VEGF to its receptor is inhibited.

2. The method of claim 1, wherein the nucleic acid ligand to VEGF is identified according to a method comprising the steps of:
   a) preparing a candidate mixture of nucleic acids;
   b) contacting the candidate mixture with VEGF, wherein nucleic acids having an increased affinity to VEGF relative to the candidate mixture may be partitioned from the remainder of the candidate mixture;
   c) partitioning the increased affinity nucleic acids from the remainder of the candidate mixture; and
   d) amplifying the increased affinity nucleic acids to yield a ligand-enriched mixture of nucleic acids, whereby a VEGF nucleic acid ligand may be identified.

3. The method of claim 1, wherein said VEGF nucleic acid ligand is a ribonucleic acid.

4. The method of claim 1, wherein said VEGF nucleic acid ligand is a deoxyribonucleic acid.

5. The method of claim 1, wherein said VEGF nucleic acid ligand comprises modified nucleotides.

6. The method of claim 5, wherein said VEGF ligand is comprised of 2'-amino (2'-NH$_2$) modified nucleotides and 2'-O-methyl (2'-OMe) modified nucleotides.

7. The method of claim 1, wherein said VEGF nucleic acid ligand is modified with a moiety that decreases the activity of endonucleases or exonucleases on the nucleic acid ligand relative to the unmodified nucleic acid ligand, without adversely affecting the binding affinity of said nucleic acid ligand.

8. The method of claim 7, wherein said moiety comprises a phosphorothioate nucleotide.

9. The method of claim 1, wherein said VEGF nucleic acid ligand is modified by a method comprising substituting nucleotide residues, wherein said residues may be chemically modified, and wherein the modification decreases the activity of endonucleases or exonucleases relative to the unmodified nucleic acid ligand, without adversely affecting the binding affinity of said nucleic acid ligand.

* * * * *